(12) United States Patent
Fujiwara et al.

(10) Patent No.: US 7,572,911 B2
(45) Date of Patent: Aug. 11, 2009

(54) AZO COMPOUND AND PROCESS OF PRODUCING THE SAME, AND NOVEL COMPOUND AND PROCESS OF PRODUCING AZO COMPOUNDS USING THE SAME

(75) Inventors: Toshiki Fujiwara, Kanagawa (JP); Naoyuki Hanaki, Kanagawa (JP); Shigeaki Tanaka, Kanagawa (JP); Tadashi Omatsu, Kanagawa (JP); Yoshiharu Yabuki, Kanagawa (JP)

(73) Assignee: Fujifilm Corporation, Minato-Ku, Tokyo (JP)

( * ) Notice: Subject to any disclaimer, the term of this patent is extended or adjusted under 35 U.S.C. 154(b) by 0 days.

(21) Appl. No.: 11/433,484

(22) Filed: May 15, 2006

(65) Prior Publication Data

US 2007/0173641 A1 Jul. 26, 2007

Related U.S. Application Data

(62) Division of application No. 10/473,419, filed as application No. PCT/JP02/03491 on Apr. 8, 2002, now Pat. No. 7,109,336.

(30) Foreign Application Priority Data

| Apr. 9, 2001 | (JP) | ............................ P.2001-110458 |
| Apr. 24, 2001 | (JP) | ............................ P.2001-126239 |
| Jan. 21, 2002 | (JP) | ............................ P.2002-012108 |

(51) Int. Cl.
C07D 213/72 (2006.01)
C07D 241/20 (2006.01)

(52) U.S. Cl. ........................................ 544/336; 546/307
(58) Field of Classification Search .................. 544/336; 546/307

See application file for complete search history.

(56) References Cited

U.S. PATENT DOCUMENTS 3,573,272 A 3/1971 Voltz et al.

5,144,015 A 9/1992 Chapman

FOREIGN PATENT DOCUMENTS

| DE | 23 52 831 A1 | 4/1975 |
| GB | 1 420 987 | 1/1976 |
| JP | 50-73920 A | 6/1975 |
| JP | 5-96869 A | 4/1993 |
| JP | 6-19036 A | 3/1994 |

OTHER PUBLICATIONS

Jakob Jerchel, Databasae Crossfire Beilstein 'Online!; Beilstein Institut zur Förderung der Chemischen Wissenschaften, Frankfurt am Main, DE, XP-002216816, Chem. Ber., 92, 1959 (abstract).

Tilman, Wibaut, Databasae Crossfire Beilstein 'Online!; Beilstein Institut zur Förderung der Chemischen Wissenschaften, Frankfurt am Main, DE, XP-002216817, Recl. Trav. Chim. Pays-Bas; 52, 1933 (abstract).

Von Bedenburg et al., Databasae Crossfire Beilstein 'Onlin!; Beilstein Institut zur Förderung der Chemischen Wissenschaften, Frankfurt am Main, DE, XP-002216818, Chem. Ztg.; 103; 1979 (abstract).

*Primary Examiner*—Taofiq A Solola
(74) *Attorney, Agent, or Firm*—Buchanan Ingersoll & Rooney PC

(57) ABSTRACT

A compound represented by the following formula (I) or formula (2-I):

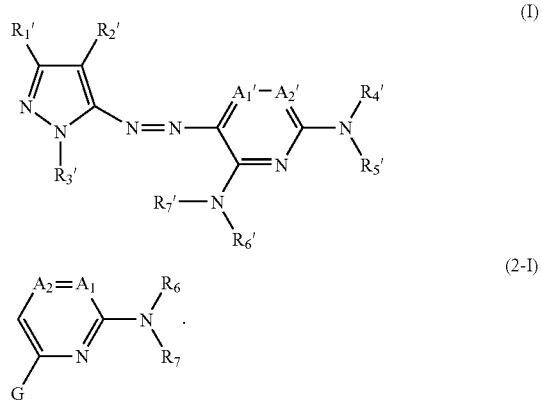

4 Claims, No Drawings

AZO COMPOUND AND PROCESS OF PRODUCING THE SAME, AND NOVEL COMPOUND AND PROCESS OF PRODUCING AZO COMPOUNDS USING THE SAME

CROSS-REFERENCE TO RELATED APPLICATIONS

This application is a divisional of application Ser. No. 10/473,419, filed Sep. 30, 2003 now U.S. Pat. No. 7,109,336, the contents of which are incorporated herein by reference, which in turn was the National Stage of International Application No. PCT/JP02/03491 filed Apr. 8, 2002.

FIELD OF THE INVENTION

This invention relates to a novel azo compound and a process for producing the same, and a novel compound used to produce an azo compound suitable as a dye and a process for producing an azo compound using the novel compound.

BACKGROUND OF THE INVENTION

Color image recording materials have come to prevail over black-and-white image recording materials. They have found use in several applications, such as in ink jet recording, heat transfer recording, electrophotography, transfer type silver halide photographic materials, printing inks, recording pens, and color filters in displays, such as liquid crystal displays and plasma display panels, and solid-state image sensors, such as charge coupled device (CCD) image sensors.

These color image recording materials and color filters use colorants (dyes and pigments) of additive or subtractive primaries to implement full color reproduction or recording. Nevertheless, colorants having absorption characteristics suitable for favorable color reproduction and fastness against various conditions of use are not currently available.

Ink jet recording has rapidly become popular and will see further development because of low material cost, high speed, low noise, and ease of color recording. Fundamentally, ink jet recording is divided into a continuous method in which ink droplets are continuously allowed to fly and a drop-on-demand method in which ink droplets are made to fly upon image information signals. The mechanism of drop formation includes a piezoelectric system in which pressure is applied to ink by a piezoelectric element to eject ink droplets, a thermal system in which an air bubble is generated by heat to eject ink droplets, an acoustic system, and an electrostatic system in which ink droplets are sucked or ejected by an electrostatic force. Ink-jet inks include aqueous ink, oily ink, and solid ink (melting type).

Colorants used in ink-jet inks are required to have (1) good solubility or dispersibility in ink solvents, (2) capability of forming a high-density image, (3) satisfactory hues, (4) fastness against light, heat, and active gases in the environment (e.g., $NO_x$, oxidizing gases such as ozone, $SO_x$, etc.), (5) resistance against water or chemicals, (6) good fixability on media with minimized feathering, (7) stability in ink formulations, (8) nontoxicity, (9) high purity, and (10) inexpensiveness. It is extremely difficult to obtain colorants meeting all these requirements. In particular, colorants having both a favorable magenta hue and fastness to light and active gases in the environment, particularly oxidizing gases such as ozone, have been eagerly sought.

Coupling components for azo dyes that have been widely used include phenols, naphthols, and anilines. JP-A-11-209673 (The term "JP-A" as used herein means an "unexamined published Japanese patent application") and Japanese Patent 3020660 disclose azo dyes obtained by using these coupling components, which have satisfactory hues but poor light fastness. Japanese Patent Application No. 2000-220649 proposed dyes with satisfactory hues and improved light fastness. However, all the colorants known by the literature are extremely unsatisfactory in fastness to oxidizing gases such as ozone.

In seeking for dyes with satisfactory fastness to oxidizing gases such as ozone, the present inventors have arrived at the idea of using a nitrogen-containing heterocyclic compound as a coupling component, dropping the idea of using the conventional coupling components such as phenols, naphthols, and anilines. Azo dyes made from an aminopyrazole diazo component and an aniline coupling component are disclosed in JP-A-55-161856, JP-A-61-36362, JP-A-61-152768, JP-A-6-145543, JP-A-7-224230, U.S. Pat. Nos. 4,650,861 and 4,301,070, and JP-W-11-504958 (The term "JP-W" as used herein means an "international patent application published in the Japanese national proceeding"). As stated above, none of the conventional techniques has succeeded in furnishing azo dyes satisfactory in both hue and fastness. Azo dyes comprising a pyridine coupling component are known as disclosed in JP-A-51-83631, JP-A-49-74718, JP-A-58-101158, JP-B-52-46230 (The term "JP-B" as used herein means an "examined Japanese patent application"), European Patent 23309, and German Patents 2719079, 2307444, 2513949, 2525505, and 2832020. Azo dyes comprising a pyrazole diazo component and a pyridine coupling component are utterly unknown.

Azo dyes composed of a pyrazole diazo component and an aniline coupling component have been synthesized according to the processes taught, e.g., in U.S. Pat. Nos. 3,336,285 and 3,639,384 and British Patent 1,566,985. The process of the U.S. Patents comprises diazotizing a 1-alkyl-4-cyano-5-aminopyrazole followed by coupling reaction to produce a 1-alkyl-4-cyanopyrazol-5-yl azo pigment. However, a diazonium salt used in the process is very labile, causing difficulty in obtaining dyes in high yield and with high purity through diazotization and coupling (see Weaver and Shuttleworth, *Dyes and Pigments*, vol. 3, p. 81 (1982)). 1-Alkyl-3-(secondary or tertiary alkyl)-4-cyanopyrazol-5-ylazo dyes synthesized by the process disclosed in JP-B-6-19036 have hues of short wavelengths and are unsatisfactory as magenta dyes.

The process proposed in British Patent 1,566,985 supra comprises subjecting a 1-alkyl-3-alkyl(or aryl)-4-halogeno-5-aminopyrazole and an aromatic coupling component to diazotization and coupling and substituting the halogen at the 4-position with —CN to synthesize a 1-alkyl-3-alkyl(or aryl)-4-cyanopyrazol-5-ylazo dye. Using a heavy metal cyanide, e.g., CuCN or $Zn(CN)_2$, the process involves such issues as waste disposal and purification of produced dyes.

A process for producing an azo dye comprising a pyrazole diazo component and a pyridine coupling component with ease and in high yield is unknown. Known processes applicable to synthesis of the compound of the present invention have many drawbacks. In addition, introducing an arbitrary substituent to the amino group of the pyridine moiety of a dye compound represented by formula (I-H1) according to the invention has been often accompanied with heat elevation or has often involved a complicated reaction system which makes product isolation difficult. Moreover, it is unknown how to water-solubilize an azo dye comprising a pyrazole diazo component and a pyridine coupling component with ease and in high yield.

SUMMARY OF THE INVENTION

An object of the present invention is:

I) to provide an organic compound having a specific structure which is useful in chemistry, agriculture, medicine or the like or an intermediate therefore;

II) to provide a novel dye having excellent absorption characteristics suitable for favorable color reproduction as one of three primary colors and sufficient fastness to light, heat, humidity, and active gases in the environment, and a process of producing the same;

III) to provide coloring compositions providing color images or coloring materials excellent in hue and fastness in broad applications, such as printing ink compositions for, for example, ink jet printing; ink sheets used in thermal transfer image forming materials; toners for electrophotography; coloring compositions for color filters used in solid-state image sensors such as CCDs; and dye baths for textile;

IV) to provide an ink composition for ink jet recording which is capable of forming an image with a satisfactory hue and high fastness to light and active gases in the environment, especially ozone; and V) to provide a novel compound suitable for the production of azo compounds which exhibit excellent color reproducibility and sharp absorption characteristics with a narrow half-value width as a dye of three primary colors and to provide a process of producing an azo compound in high yield by using the novel compound.

In seeking dyes with a good hue and fastness, the present inventors have found that the above objects of the invention can be accomplished by a first aspect of the invention (the first aspect includes following items 1) to 10)), that is, an azo compound with a heretofore unknown specific dye skeleton, represented by formula (I) shown below, a process of producing the compound, and a coloring composition containing the compound.

1) A compound represented by formula (I):

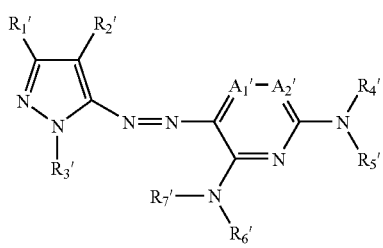

(I)

wherein $R_1'$ represents a hydrogen atom, an alkyl group, a cycloalkyl group, an aralkyl group, an aryl group, a heterocyclic group or an acyl group, wherein each group may have a substituent; $R_2'$ represents a hydrogen atom, a halogen atom or a cyano group; $R_3'$ represents a hydrogen atom, an alkyl group, a cycloalkyl group, an aralkyl group, an alkenyl group, an aryl group, a heterocyclic group, a carboxyl group or a sulfo group, wherein each group may have a substituent; $R_4'$, $R_5'$, $R_6'$, and $R_7'$ each represent a hydrogen atom, an alkyl group, a cycloalkyl group, an aralkyl group, an alkenyl group, an aryl group, a heterocyclic group, a sulfonyl group, an acyl group, a carboxyl group, a sulfo group or a carbamoyl group, wherein each group may have a substituent, provided that $R_4'$ and $R_5'$ do not simultaneously represent a hydrogen atom and that $R_6'$ and $R_7'$ do not simultaneously represent a hydrogen atom; and $A_1'$ and $A_2'$ each represent —CR= or a nitrogen atom provided that $A_1'$ and $A_2'$ do not simultaneously represent a nitrogen atom wherein R represents a hydrogen atom or a substituent.

2) A preferred group of the compounds represented by formula (I) are represented by formula (I-R1):

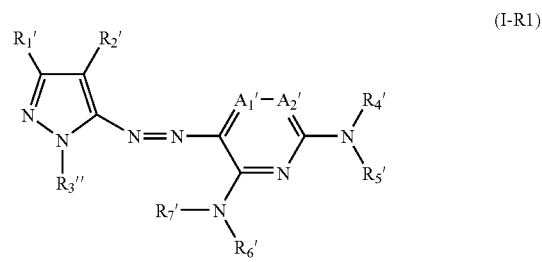

(I-R1)

wherein $R_1'$, $R_2'$, $R_4'$, $R_5'$, $R_6'$, $R_7'$, $A_1'$, and $A_2'$ are as defined above; and $R_3''$ of formula (I-R1) represents an alkyl group, a cycloalkyl group, an aralkyl group, an alkenyl group, an aryl group or a heterocyclic group.

3) The compound represented by formula (I-R1) preferably includes a compound represented by formula (I-R2):

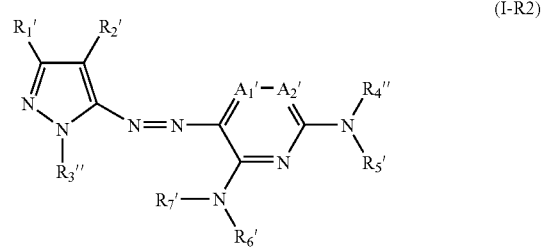

(I-R2)

wherein $R_1'$, $R_2'$, $R_3''$, $R_5'$, $R_6'$, $R_7'$, $A_1'$, and $A_2'$ of formula (I-R2) are as defined in formula (I-R1); and $R_4''$ of formula (I-R2) represents a substituted or unsubstituted alkyl group, a substituted or unsubstituted cycloalkyl group, a substituted or unsubstituted aralkyl group, a substituted or unsubstituted alkenyl group, a substituted or unsubstituted aryl group, a substituted or unsubstituted heterocyclic group, a carboxyl group or a sulfo group.

4) The compound represented by formula (I-R1) preferably includes a compound represented by formula (I-R3):

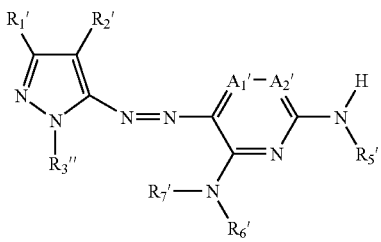

(I-R3)

wherein $R_1'$, $R_2'$, $R_3''$, $R_5'$, $R_6'$, $R_7'$, $A_1'$, and $A_2'$ of formula (I-R3) are as defined in formula (I-R1).

5) The compound represented by formula (I-R1) preferably includes a compound represented by formula (I-R4):

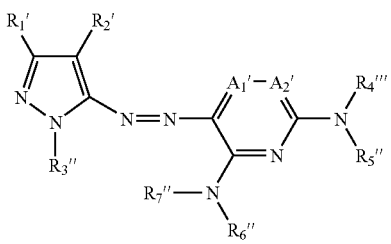

(I-R4)

wherein $R_1'$, $R_2'$, $R_3''$, $A_1'$, and $A_2'$ of formula (I-R4) are as defined in formula (I-R1); and $R_4'''$, $R_5''$, $R_6''$, and $R_7''$ of formula (I-R4) each represent a hydrogen atom, an alkyl group, a cycloalkyl group, an aralkyl group, an alkenyl group, an aryl group, a heterocyclic group, a sulfonyl group, an acyl group or a carbamoyl group.

6) A preferred group of the compounds represented by formula (I) are represented by formula (I-H1):

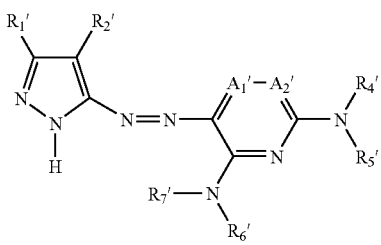

(I-H1)

wherein $R_1'$, $R_2'$, $R_4'$, $R_5'$, $R_6'$, $R_7'$, $A_1'$, and $A_2'$ are as defined above.

7) The compound represented by formula (I-H1) is preferably represented by formula (I-H2):

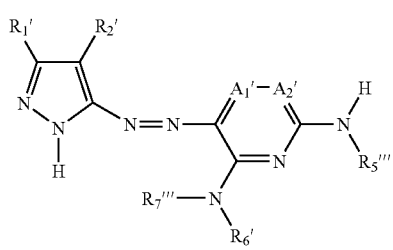

(I-H2)

wherein $R_1'$, $R_2'$, $R_6'$, $A_1'$, and $A_2'$ are as defined above; and $R_5'''$ and $R_7'''$ of formula (I-H2) each represent an alkyl group, a cycloalkyl group, an aralkyl group, an alkenyl group, an aryl group, a heterocyclic group, a sulfonyl group, an acyl group, a carboxyl group, a sulfo group or a carbamoyl group, each of which may have a substituent.

8) The invention also provides processes of producing the compound of formula (I-R1). One of the processes comprises the steps of:
(a) allowing an aminopyrazole derivative represented by formula (II):

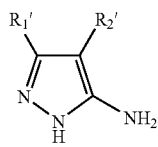

(II)

wherein $R_1'$ and $R_2'$ are as defined above,
and a diazotizing agent to react to form a diazonium salt,
(b) allowing the diazonium salt to react with a coupling component represented by formula (III):

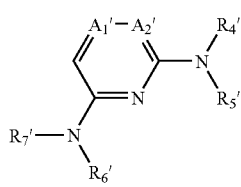

(III)

wherein $R_4'$, $R_5'$, $R_6'$, $R_7'$, $A_1'$, and $A_2'$ are as defined above, to form a compound represented by formula (I-H1), and
(c) allowing the compound represented by formula (I-H1) to react with an alkylating agent, an arylating agent or a heterylating agent in the presence of a base. Another process comprises the step of introducing a water-soluble group by an electrophilic reaction into a compound represented by formula (I-R4).

9) In the process of item 8) above, the electrophilic reaction is sulfonation.

10) The present invention also provides processes for producing the compound represented by formula (I-R2). One of the processes comprises allowing a compound represented by formula (I-H1) to react with an alkylating agent, an arylating agent or a heterylating agent under an oxygen-free condition. The other process for producing the compound represented by formula (I-R2) comprises the steps of:

allowing a compound represented by formula (I-H2) to react with an alkylating agent, an arylating agent or a heterylating agent to form a compound represented by formula (I-R3) and allowing the compound represented by formula (I-R3) to react with an alkylating agent, an arylating agent or a heterylating agent under an oxygen-free condition.

In addition, the present inventors have conducted research concerning dye derivatives in an attempt to obtain dyes with satisfactory hues. As taught by Sumio Tokita in *Chemical Seminar 9 Color Chemistry*, pp. 150-161, Maruzen (1982), hues are always influenced by not only the energy level of electrons but the levels of molecular vibration or rotation. It is expected therefore that reduction of the influences by molecular vibration or rotation will make an absorption band narrower and sharper (with a narrower half-value width).

In order to sharpen a hue, it is necessary to suppress the rotation around the bond between the aromatic group or heterocyclic group as $R_6$ or $R_7$ and the nitrogen atom in formula (2-I). That is, where one of $R_6$ and $R_7$ is an aromatic or heterocyclic group with the other being a substituent other than a hydrogen atom, the aromatic or heterocyclic group undergoes steric hindrance by that substituent so that rotation of the aromatic or heterocyclic group is suppressed.

Where one of $R_6$ and $R_7$ is a hydrogen atom, the aromatic or heterocyclic group must satisfy either condition (i) that it has a substituent on a position next to the carbon atom bonded to the nitrogen atom (to which $R_6$ and $R_7$ are bonded) or condition (ii) that the above-described position has a non-covalent bonding electron pair like a nitrogen atom.

By any of the above-described configurations, the aromatic group or the heterocyclic group as $R_6$ or $R_7$ is in a staggered conformation relative to the plane of the pyridine ring, pyrimidine ring or pyrazine ring and thereby inhibited from rotating. It has been confirmed in practice that azo compounds prepared by using the compound of formula (2-I) are free from the above-mentioned hue problems.

In the preparation of an azo compound starting with the compound of formula (2-I), a better yield resulted when the azo compound is completely dissolved in the system or when the reaction is carried out in a water/organic solvent two-layer system. The inventors have also found that converting a diazo component to a diazonium salt attains a markedly improved yield by using hydrochloric acid-sodium nitrite, isopentyl nitrite or nitrosylsulfuric acid, which are environmentally friendly diazotizing reagents. The present invention has been completed based on these findings.

The above objects of the invention are accomplished by a second aspect of the invention including following items 11) to 13).

11) The present invention provides a compound represented by formula (2-I):

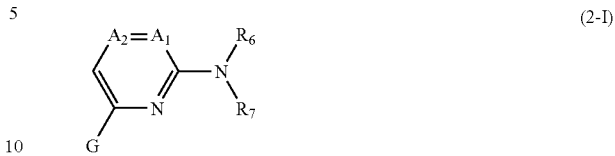

(2-I)

wherein $A_1$ represents —$CR_1$═ or a nitrogen atom and $A_2$ represents —$CR_2$═ or a nitrogen atom provided that $A_1$ and $A_2$ do not simultaneously represent a nitrogen atom; at least one of $R_6$ and $R_7$ represents an aromatic group or a heterocyclic group with the other representing a hydrogen atom, an aliphatic group, an aromatic group, a heterocyclic group, an acyl group, an alkoxycarbonyl group, an aryloxycarbonyl group or a sulfamoyl group, wherein each group may have a substituent; G, $R_1$, and $R_2$ each represent a hydrogen atom, a halogen atom, an aliphatic group, an aromatic group, a heterocyclic group, a cyano group, a carboxyl group, a carbamoyl group, an alkoxycarbonyl group, an aryloxycarbonyl group, an acyl group, a hydroxyl group, an alkoxy group, an aryloxy group, a silyloxy group, an acyloxy group, a carbamoyloxy group, a heterocyclic oxy group, an alkoxycarbonyloxy group, an aryloxycarbonyloxy group, an amino group substituted with an alkyl group, an aromatic group or a heterocyclic group, an acylamino group, a ureido group, a sulfamoylamino group, an alkoxycarbonylamino group, an aryloxycarbonylamino group, an alkylsulfonylamino group, an arylsulfonylamino group, a nitro group, an alkylthio group, an arylthio group, a heterocyclic thio group, an alkylsulfonyl group, an arylsulfonyl group, an alkylsulfinyl group, an arylsulfinyl group, a sulfamoyl group or a sulfo group, wherein each group may have a substituent, provided that G is not an alkyl-substituted amino group when $A_1$ and $A_2$ represent —$CR_1$═ and —$CR_2$═ respectively; or $R_1$ and $R_6$ are taken together, or $R_6$ and $R_7$ are taken together, each to form a 5- or 6-membered ring.

12) The compound represented by formula (2-I) is preferably represented by formula (2-II):

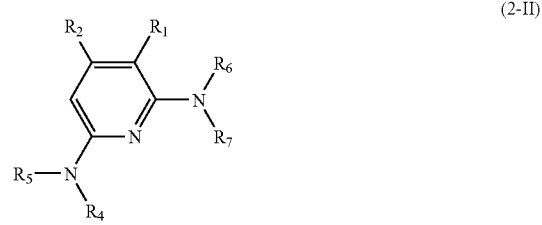

(2-II)

wherein $R_1$, $R_2$, $R_6$, and $R_7$ are as defined above; and at least one of $R_4$ and $R_5$ represents an aromatic group or a heterocyclic group with the other representing a hydrogen atom, an aromatic group, a heterocyclic group, an acyl group, an alkoxycarbonyl group, an aryloxycarbonyl group, a carbamoyl group, a sulfonyl group, and a sulfamoyl group, wherein the group represented by $R_1$, $R_2$, $R_4$, $R_5$ or $R_6$ may have a substituent.

13) The present invention also provides a process of producing an azo compound comprising allowing the compound of formula (2-I), preferably the compound of formula (2-II), to react with a diazonium salt formed by a diazotizing agent.

DETAILED DESCRIPTION OF THE INVENTION

The First Aspect of the Invention

The compounds of formula (I) according to the invention preferably include compounds of formula (I-R1) and compounds of formula (I-H1). The compounds of formula (I-R1) preferably include those of formulae (I-R2), (I-R3), and (I-R4). The compounds of formula (I-H1) preferably include those of formula (I-H2).

In formula (I), $R_1'$ represents a hydrogen atom, an alkyl group, a cycloalkyl group, an aralkyl group, an aryl group, a heterocyclic group or an acyl group, wherein each group may have a substituent.

The term "alkyl group" is intended to include a substituted alkyl group and an unsubstituted alkyl group. The alkyl group preferably contains 1 to 12 carbon atoms, particularly 1 to 6 carbon atoms, as unsubstituted. Substituents for the alkyl group include a hydroxyl group, an alkoxy group, a cyano group, a halogen atom, and an ionic hydrophilic group. Examples of the alkyl group are methyl, ethyl, butyl, isopropyl, t-butyl, hydroxyethyl, methoxyethyl, cyanoethyl, trifluoromethyl, 3-sulfopropyl, and 4-sulfobutyl.

The term "cycloalkyl group" is intended to include a substituted one and an unsubstituted one. The cycloalkyl group preferably has 5 to 12 carbon atoms as unsubstituted. Substituents on the cycloalkyl group include ionic hydrophilic groups. Examples of the cycloalkyl group are a cyclohexyl group.

The term "aralkyl group" includes a substituted aralkyl group and an unsubstituted one. The aralkyl group, as unsubstituted, preferably has 7 to 12 carbon atoms. The substituents on the aralkyl group include ionic hydrophilic groups. Examples of the aralkyl group are a benzyl group and a 2-phenethyl group.

The term "aryl group" means a substituted or unsubstituted aryl group. The aryl group preferably has 6 to 12 carbon atoms. Substituents for the aryl group include an alkyl group, an alkoxy group, a halogen atom, an alkylamino group, an amido group, a carbamoyl group, a sulfamoyl group, a sulfonamido group, a hydroxyl group, an ester group, and an ionic hydrophilic group. The aryl group includes phenyl, p-tolyl, p-methoxyphenyl, o-chlorophenyl, and m-(3-sulfopropylamino)phenyl.

The term "heterocyclic group" is used to describe a substituted or unsubstituted heterocyclic group. The heterocyclic group is preferably 5- or 6-membered. Suitable substituents on the heterocyclic group include an amido group, a carbamoyl group, a sulfamoyl group, a sulfonamido group, a hydroxyl group, an ester group, and an ionic hydrophilic group. Suitable examples of the heterocyclic group are 2-pyridyl, 2-thienyl, 2-thiazolyl, 2-benzothiazolyl, and 2-furyl.

The term "acyl group" includes a substituted acyl group and an unsubstituted acyl group. An acyl group having 1 to 12 carbon atoms as unsubstituted is preferred. The substituents for the acyl group include ionic hydrophilic groups. Suitable examples of the acyl group are an acetyl group and a benzoyl group.

$R_2'$ represents a hydrogen atom, a halogen atom or a cyano group.

$R_4'$, $R_5'$, $R_6'$, and $R_7'$ each represent a hydrogen atom, an alkyl group, a cycloalkyl group, an aralkyl group, an alkenyl group, an aryl group, a heterocyclic group, a sulfonyl group, an acyl group, a carboxyl group, a sulfo group or a carbamoyl group, wherein each group may have a substituent.

The definitions of the terms "alkyl group", "cycloalkyl group", "aralkyl group", "aryl group", "heterocyclic group", and "acyl group" and their preferred ranges described with respect to $R_1'$ apply to $R_4'$, $R_5'$, $R_6'$, and $R_7'$.

The term "alkenyl group" includes a substituted alkenyl group and an unsubstituted one. An alkenyl group having 5 to 12 carbon atoms as unsubstituted is preferred. Substituents for the alkenyl group include ionic hydrophilic groups. Examples of the alkenyl group are a vinyl group and an allyl group.

The sulfonyl group includes an alkylsulfonyl group, e.g., methanesulfonyl, and an arylsulfonyl group, e.g., phenylsulfonyl.

$R_4'$ and $R_5'$ do not simultaneously represent a hydrogen atom. $R_6'$ and $R_7'$ do not simultaneously represent a hydrogen atom, either.

$R_3'$ represents a hydrogen atom, an alkyl group, a cycloalkyl group, an aralkyl group, an alkenyl group, an aryl group, a heterocyclic group, a carboxyl group or a sulfo group, wherein each group may have a substituent. Particulars of these groups are the same as those described for $R_4'$, $R_5'$, $R_6'$, and $R_7'$.

$A_1'$ and $A_2'$ each represent —CR= or a nitrogen atom provided that $A_1'$ and $A_2'$ do not simultaneously represent a nitrogen atom wherein R represents a hydrogen atom or a substituent. The substituents of the substituted carbon atom include those described with respect to $R_4'$, $R_5'$, $R_6'$, and $R_7'$.

Examples of preferred substituents as represented by $R_1'$, $R_2'$, $R_3'$, $R_4'$, $R_5'$, $R_6'$, $R_7'$, $A_1'$, and $A_2'$ in formula (I) are as follows.

$R_1'$ is preferably an alkyl group or an aryl group. The alkyl group as $R_1'$ is preferably an isopropyl group or a t-butyl group. The aryl group as $R_1'$ is preferably a phenyl group or a phenyl group having a substituent at the 2-, 4- or 6-position with respect to the pyrazole nucleus.

$R_2'$ is preferably a cyano group.

$R_3'$ is preferably an aryl group substituted with an electron-attracting group, a heterocyclic group or a heterocyclic group substituted with an electron-attracting group. The electron-attracting group has a Hammett's substituent constant σp value of 0.20 or greater, preferably 0.30 or greater. The upper limit of the σp value is preferably 1.0. The Hammett's substituent constant σp value is explained here briefly. Hammett's rule is a rule of thumb proposed by L. P. Hammett in 1935 in an attempt to discuss quantitatively the influences of substituents on reaction and equilibrium of benzene derivatives and is today generally admitted to be valid. Substituent constants used in Hammett's rule include a σp value and a σm value. These values are found in many general books, such as J. A. Dean (ed.), *Lange's Handbook of Chemistry,* 12th Ed., McGraw-Hill (1979) and *Kagaku-no-ryoiki*, Extra No. 122, pp. 96-103, Nankodo (1979). In the present invention various substituents will be limited or described in terms of Hammett's substituent constant σp. This does not mean that intended substituents are limited to those substituents the σp value of which is known from literature, and intended substituents include any substituent of which the σp value is not found in literature but seems to fall within a recited range when measured based on Hammett's rule.

Electron-attracting groups having a σp value of 0.20 or greater include an acyl group, an acyloxy group, a carbamoyl group, an alkyloxycarbonyl group, an aryloxycarbonyl group, a cyano group, a nitro group, a dialkylphosphono group, a diarylphosphono group, a diarylphosphinyl group, an alkylsulfinyl group, an arylsulfinyl group, an alkylsulfonyl group, an arylsulfonyl group, a sulfonyloxy group, an acylthio group, a sulfamoyl group, a thiocyanate group, a thiocarbonyl group, a halogenated alkyl group, a halogenated alkoxy group, a halogenated aryloxy group, a halogenated alkylamino group, a halogenated alkylthio group, a heterocyclic group, a halogen atom, an azo group, a selenocyanate group, and an aryl group substituted with an electron-attracting group having a σp value of 0.20 or greater. Of the above, a cyano group, a nitro group, and a halogen atom are preferred.

As previously defined, $A_1'$ and $A_2'$ each represent —CR═ or a nitrogen atom provided that $A_1'$ and $A_2'$ do not simultaneously represent a nitrogen atom wherein R represents a hydrogen atom or a substituent. It is preferred that $A_1'$ and $A_2'$ both represent —CR═ for better performance.

Of the substituents of the substituted carbon atom, preferred are an alkyl group having 1 to 3 carbon atoms, a carboxyl group, a carbamoyl group, and a cyano group.

$R_4'$, $R_5'$, $R_6'$, and $R_7'$ each preferably represent a hydrogen atom, an alkyl group having 1 to 8 carbon atoms, an aryl group, a sulfonyl group, an acyl group or a heterocyclic group. More preferably, they represent a sulfonyl group, an acyl group, an aryl group or a heterocyclic group. $R_4'$ and $R_5'$ do not simultaneously represent a hydrogen atom. $R_6'$ and $R_7'$ do not simultaneously represent a hydrogen atom, either.

Where it is desired for the compound of formula (I) to be water-soluble, it is preferred that at least two, particularly at least three, of $R_3'$, $R_4'$, $R_5'$, $R_6'$, and $R_7'$ have a sulfo group or a carboxyl group.

The compound of formula (I-R1) is prepared by process (A) comprising the steps of:

(a) allowing an aminopyrazole derivative represented by formula (II) and a diazotizing agent to react to form a diazonium salt, (b) allowing the diazonium salt to react with a coupling component represented by formula (III) to form a compound represented by formula (I-H1), and (c) allowing the compound represented by formula (I-H1) to react with an alkylating agent, an arylating agent or a heterylating agent in the presence of a base, or process B comprising the step of:

introducing a water-soluble group by an electrophilic reaction into a compound represented by formula (I-R4).

The diazotizing agent which can be used in step (a) of process A includes a diluted hydrochloric acid solution of sodium nitrite, isopentyl nitrite, and nitrosylsulfuric acid, with a dilute hydrochloric acid solution of sodium nitrite being preferred.

In formula (III) representing the coupling component used in step (b) of process A, preferred examples of $A_1'$, $A_2'$, $R_4'$, $R_5'$, $R_6'$, and $R_7'$ are the same as those recited with reference to formula (I).

The alkylating agent, arylating agent or heterylating agent used in step (c) of process A is represented by formula (IV), (V) or (VI), respectively.

R—X                                    (IV)

Ar—X                                   (V)

Het—X                                  (VI)

In formula (IV), R represents a substituted or unsubstituted alkyl group; and X represents a halogen atom or $OSO_2R'$, wherein R represents an alkyl group or an aryl group (e.g., phenyl).

In formula (V), Ar represents a phenyl group substituted with an electron-attracting group, preferably a phenyl group substituted with an electron-attracting group having a Hammett's σp value of 0.2 or greater.

In formula (VI), Het represents a heterocyclic group, preferably a 2-pyridyl group, a 2-thienyl group, a 2-thiazolyl group, a 2-benzothiazolyl group, a triazyl group or a 2-furyl group.

The base used in step (c) includes organic bases, such as diisopropylethylamine; and inorganic bases, such as potassium carbonate, sodium carbonate, sodium hydrogencarbonate, potassium hydrogencarbonate, sodium hydroxide, and potassium hydroxide.

The electrophilic reaction usable in process B includes sulfonation, Mannich reaction, and Friedel-Crafts reaction, with sulfonation being preferred.

Sulfonation of the compound of formula (I-R4) is carried out with concentrated sulfuric acid, 10 to 60% fuming sulfiric acid, chlorosulfonic acid, sulfur trioxide, amidosulfuric acid, etc. as a sulfonating agent with or without a solvent. Useful solvents include acetic acid, acetic anhydride, ethyl acetate, diethyl ether, carbon tetrachloride, and acetonitrile.

It is preferred that the compound of formula (I-R4) be sulfonated at $R_3''$, $R_4'''$, $R_5''$, $R_6''$, and $R_7''$. Where $R_3''$, $R_4'''$, $R_5''$, $R_6''$ or $R_7''$ of formula (I-R4) has a plurality of reaction sites capable of being sulfonated, the resulting sulfonated compound may be a mixture of compounds having sulfo groups on different sites. In such a case, the mixture may comprise a main compound having a sulfo group at a certain site of a certain group and a minor compound having a sulfo group at a different site of the certain group, with the proportion of the minor compound being 0.1 to 20% in terms of peak area in high-performance liquid chromatography. The reaction temperature is desirably −20° to 50° C., more desirably −5° to 30° C. The reaction time is desirably 30 minutes to 10 hours, more desirably 1 to 6 hours.

The compound represented by formula (I-R2) can be prepared by process C comprising allowing the compound of formula (I-H1) to react with an alkylating agent, an arylating agent or an heterylating agent under an oxygen-free condition or process D comprising the steps of allowing the compound of formula (I-H2) to react with an alkylating agent, an arylating agent or a heterylating agent to prepare a compound of formula (I-R3) and allowing the compound of formula (I-R3) with an alkylating agent, an arylating agent or a heterylating agent under an oxygen-free condition. The alkylating agent, the arylating agent, and the heterylating agent which can be used in processes C and D are the same as those described above.

The oxygen-free condition is desirably created by filling the reaction system with an inert gas, such as nitrogen or argon. More desirably, the reaction mixture is bubbled with such an inert gas.

The aminopyrazole derivative represented by formula (II) which is used in step (a) of process C is synthesized by processes taught, e.g., in U.S. Pat. No. 3,336,285, *Heterocycles*, vol. 20, p. 519 (1983), and JP-B-6-19036.

The pyridine coupling component represented by formula (III) which is used in step (a) of process A is synthesized by processes described, e.g., JP-A-51-83631, JP-A-49-74718, and JP-B-52-46230.

The azo compounds (azo dyes) represented by formula (I) can be synthesized through the above-mentioned processes A, B, C and D. Specific examples of the azo compounds according to the invention are shown below for illustrative purposes only but not for limitation.

TABLE 1

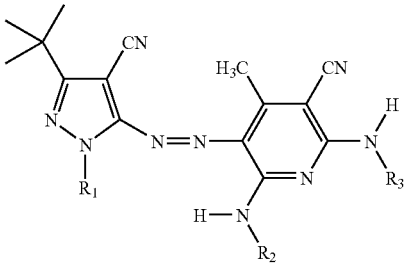

| Dye | $R_1$ | $R_2$ | $R_3$ |
|---|---|---|---|
| 1-1 | 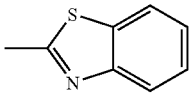 | 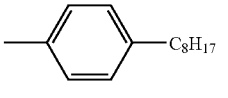 | 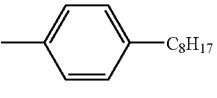 |
| 1-2 | 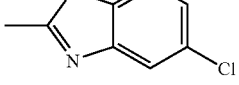 | 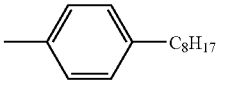 | 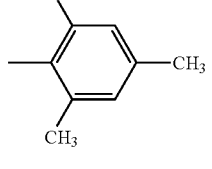 |
| 1-3 | 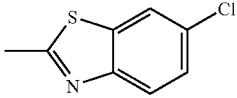 | 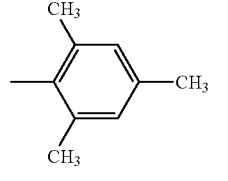 | 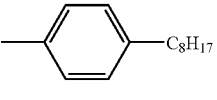 |
| 1-4 | 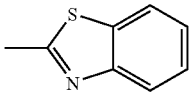 | 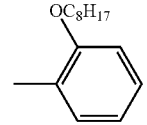 | 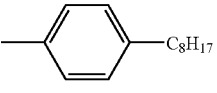 |
| 1-5 | 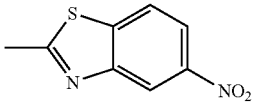 | 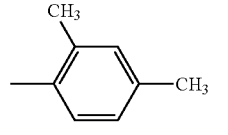 | 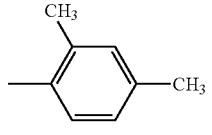 |

TABLE 1-continued

| Dye | R₁ | R₂ | R₃ |
|---|---|---|---|
| 1-6 | 2-methylbenzothiazol-6-yl-SO₂NH-(CH₂)₃-O-(2,4-di-tert-amylphenyl) | 4-methylphenyl | 4-methylphenyl |
| 1-7 | 2-methylbenzothiazol-6-yl-SO₂NH-(CH₂)₃-OCH₂CH(C₈H₁₇)(C₆H₁₃) | 2,4,6-trimethylphenyl | 4-methylphenyl |
| 1-8 | 2-methylbenzothiazol-6-yl-NHCOCH(Et)-O-(2,4-di-tert-amylphenyl) | 4-octylphenyl | 4-octylphenyl |
| 1-9 | 2-methylbenzothiazol-6-yl-NHSO₂-(2-n-octyloxy-5-tert-octylphenyl) | 2,4,6-trimethylphenyl | 4-tert-octylphenyl |
| 1-10 | 5-chloro-2-methylbenzothiazol-6-yl | 2-methyl-6-dodecyloxyphenyl | 2-methyl-6-dodecyloxyphenyl |

TABLE 2

(structure shown: pyrazole-azo-pyridine dye core with substituents R1 (on pyrazole C3), R2 (on pyrazole N1), R3 and R4 (on NH groups of pyridine); pyridine also bears CH3, CN, and two NH groups)

| Dye | R1 | R2 | R3 | R4 |
|---|---|---|---|---|
| 1-11 | tert-butyl | 2-(benzothiazolyl), 6-SO2Na | 4-methylphenyl | 4-(SO3Na)phenyl |
| 1-12 | tert-butyl | 2-(benzothiazolyl), 6-SO3Na | 2,4,6-trimethyl-3-SO3Na-phenyl | 2,4,6-trimethyl-3-SO3Na-phenyl |
| 1-13 | phenyl | 2-(benzothiazolyl), 6-COOH | 4-(SO3K)phenyl | 3-COOH-phenyl |
| 1-14 | 2-chlorophenyl | 2-(benzothiazolyl), SO3K (4,5-mix) | 4-(SO3K)phenyl | 3-COOH-phenyl |
| 1-15 | tert-butyl | 2-(benzothiazolyl), 6-SO3K | 2,4,6-trimethyl-3-SO3K-phenyl | 2,4,6-trimethyl-3-SO3K-phenyl |
| 1-16 | tert-butyl | 2-(benzothiazolyl), 6-Cl | 3,4,5-trimethyl-phenyl-CH2-N(CH2CO2H)2 | 3,4,5-trimethyl-phenyl-CH2-N(CH2CO2H)2 |
| 1-17 | tert-butyl | 2-(benzothiazolyl), 6-SO3Na | 3,4-dimethyl-5-SO3Na-phenyl | 3,4-dimethyl-5-SO3Na-phenyl |

TABLE 3
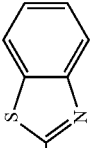
| Dye | R₁ | R₂ | R₃ | R₄ |
|---|---|---|---|---|
| 2-1 | 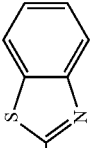 | 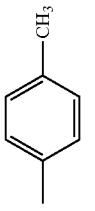 | 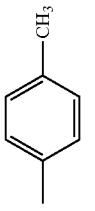 | 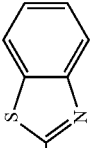 |
| 2-2 | 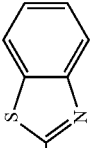 | —SO₂CH₃ | 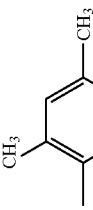 | 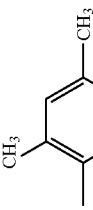 |
| 2-3 | 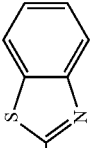 | —SO₂CH₃ | C₈H₁₇(t) | C₈H₁₇(t) |
| 2-4 | 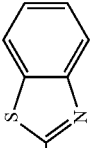 | H | 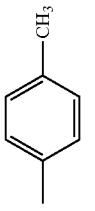 | 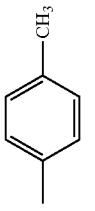 |

TABLE 3-continued
| Dye | R$_1$ | R$_2$ | R$_3$ | R$_4$ |
|---|---|---|---|---|
| 2-5 | 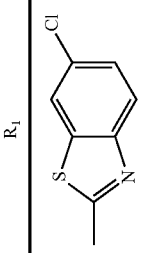 | —SO$_2$CH$_3$ |  | C$_8$H$_{17}$(t) |
| 2-6 | 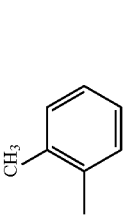 | H | 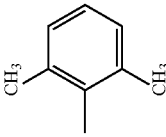 | 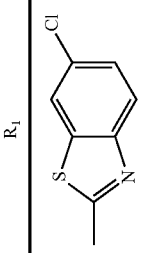 |
| 2-7 | 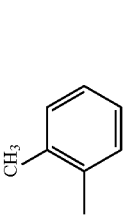 | H | 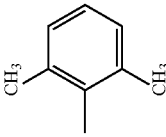 | 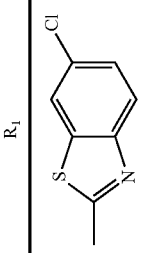 |
| 2-8 | 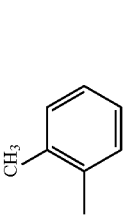 | 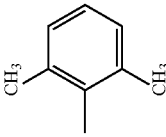 | 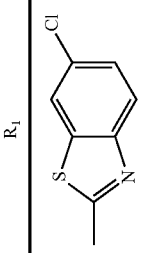 | 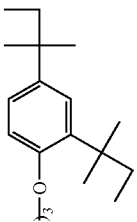 |
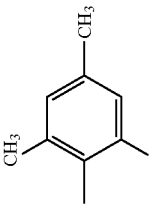

TABLE 3-continued

TABLE 3-continued

Structure:

Pyrazole-pyridine azo dye with substituents R$_1$, R$_2$, R$_3$, R$_4$; pyrazole bears CN and tert-butyl groups; pyridine bears H$_3$C and NHR$_4$, NR$_2$R$_3$.

| Dye | R$_1$ | R$_2$ | R$_3$ | R$_4$ |
|---|---|---|---|---|
| 2-13 | 2-methylbenzothiazole-6-SO$_3$K | 2-methylbenzothiazole-6-SO$_3$K | 2,4,6-trimethylphenyl | 2,4,6-trimethylphenyl |
| 2-14 | 3,5-dicarboxyphenyl-NHSO$_2$-(2-methylbenzothiazol-6-yl) | 3,5-dicarboxyphenyl-NHSO$_2$-(2-methylbenzothiazol-6-yl) | 2,4,6-trimethylphenyl | 2,4,6-trimethylphenyl |
| 2-15 | 3,5-dicarboxyphenyl-NHSO$_2$-(2-methylbenzothiazol-6-yl) (5,6-mix) | 3,5-dicarboxyphenyl-NHSO$_2$-(2-methylbenzothiazol-6-yl) (5,6-mix) | 2,4,6-trimethylphenyl | 2,4,6-trimethylphenyl |

TABLE 3-continued

| Dye | R₁ | R₂ | R₃ | R₄ |
|---|---|---|---|---|
| 2-16 | benzothiazole-SO₃Na (5,6-mix) | 3,5-dicarboxyphenyl-SO₂NH-benzothiazole (5,6-mix) | 4-methylphenyl | 2,6-dimethylphenyl |
| 2-17 | 6-SO₃Na-2-methylbenzothiazole | 6-SO₃Na-2-methylbenzothiazole | 3-SO₃Na-2,4,6-trimethylphenyl (with CH₃ at 5) | 3-SO₃Na-2,4,6-trimethylphenyl (with CH₃ at 5) |
| 2-18 | 3,5-bis(COOK)phenyl-SO₂NH-2-methylbenzothiazole | 2-methylbenzothiazole | 3-SO₃K-2,4,6-trimethylphenyl | 3-SO₃K-2,4,6-trimethylphenyl |

TABLE 3-continued

Structure:

A pyrazole-azo-pyridine dye with substituents R₁ (on pyrazole N), R₂, R₃, R₄ (on pyridine amino groups), CN on pyrazole, tert-butyl on pyrazole, and methyl (H₃C) on pyridine.

| Dye | R₁ | R₂ | R₃ | R₄ |
|---|---|---|---|---|
| 2-19 | 2-methylbenzothiazol-6-yl-SO₃Li | 2-methylbenzothiazol-6-yl-SO₃Li | 3,5-dimethyl-4-methylphenyl-SO₃Li | 3,5-dimethyl-4-methylphenyl-SO₃Li |
| 2-20 | 2-methylbenzothiazol-6-yl-SO₃Na | 2-methylbenzothiazol-6-yl-SO₃Na | 3,5-dimethyl-4-methylphenyl-CH₂N(CH₂COOH)₂ | 3,5-dimethyl-4-methylphenyl-CH₂N(CH₂COOH)₂ |
| 2-21 | 2-methylbenzothiazolyl | 2-methylbenzothiazolyl | 2,3,5-trimethyl-4-methylphenyl-SO₃K | 2,3,5-trimethyl-4-methylphenyl-SO₃K |

TABLE 3-continued
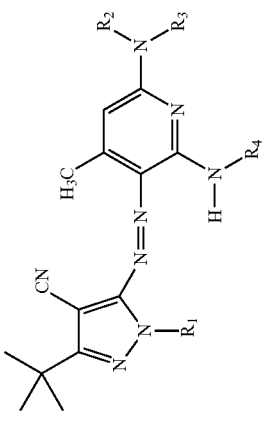
| Dye | R1 | R2 | R3 | R4 |
|---|---|---|---|---|
| 2-22 | 6-SO3K-2-methylbenzothiazolyl | 2-methylbenzothiazolyl | 2-SO3K-3,4,6-trimethylphenyl | 2-SO3K-3,4,6-trimethylphenyl |
| 2-23 | 2-methylbenzothiazolyl | 6-SO3K-2-methylbenzothiazolyl | 2-SO3K-3,4,6-trimethylphenyl | 2-SO3K-3,4,6-trimethylphenyl |

TABLE 4
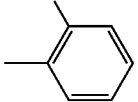
| Dye | R₁ | R₂ | R₃ | R₄ | R₅ | R₆ | R₇ | R₈ |
|---|---|---|---|---|---|---|---|---|
| 3-1 | $CH_3$ 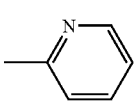 | CN | 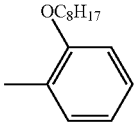 | H | $CONH_2$ | $SO_2CH_3$ | $OC_8H_{17}$ 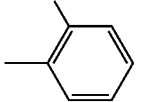 | $CH_3$  |
| 3-2 | 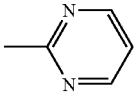 | Br | 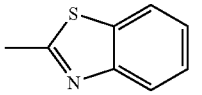 | COOEt | H | 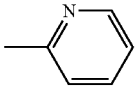 | $C_8H_{17}(t)$ | $COCH_3$ |
| 3-3 | 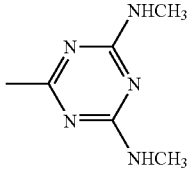 | $SO_2CH_3$ | 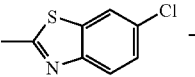 | $CONH_2$ | H |  |  | 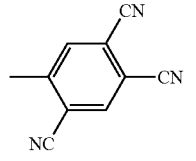 |
| 3-4 | 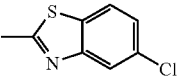 | CN | 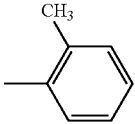 | H | H |  | 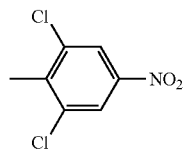 | $SO_2CH_3$ |
| 3-5 |  | Br | 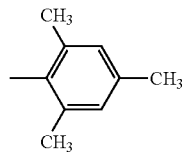 | H | $CONH_2$ | $\overset{O}{\underset{}{C}}CH_3$ | 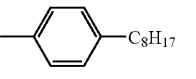 | |

TABLE 5
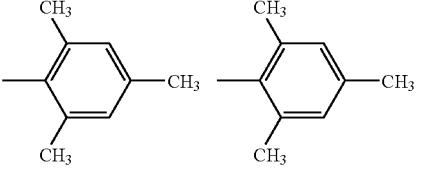
| Dye | R₁ | R₂ | R₃ |
|---|---|---|---|
| 4-1 | CN | 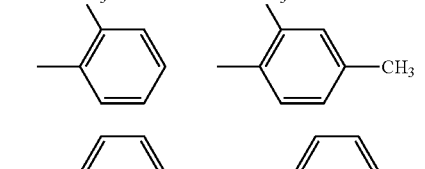 | 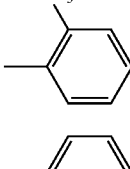 |
| 4-2 | CN | 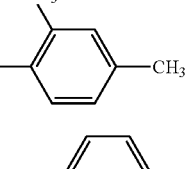 | 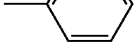 |
| 4-3 | CONH₂ | 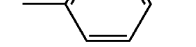 | 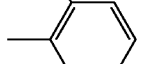 |
TABLE 5-continued
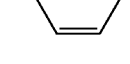
| Dye | R₁ | R₂ | R₃ |
|---|---|---|---|
| 4-4 | CONH₂ | 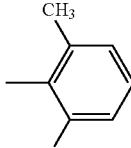 | 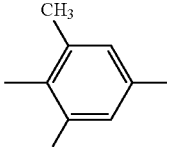 |
| 4-5 | H | 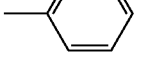 | 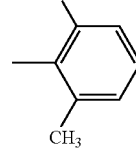 |
TABLE 6
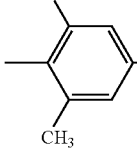
| Dye | R₁ | R₂ | R₃ | R₄ |
|---|---|---|---|---|
| 5-1 | 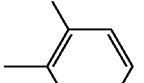 | CN | 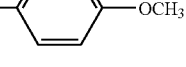 | 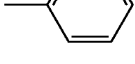 |
| 5-2 |  | CN | 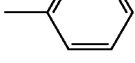 |  |
| 5-3 |  | CONH₂ | COCH₃ |  |

TABLE 6-continued

| Dye | $R_1$ | $R_2$ | $R_3$ | $R_4$ |
|---|---|---|---|---|
| 5-4 | tert-butyl | H | phenyl | $COCH_3$ |
| 5-5 | tert-butyl | H | 2,3-dimethylphenyl | 2-methylphenyl |

TABLE 7

| Dye | $R_1$ | $R_2$ | $R_3$ |
|---|---|---|---|
| 6-1 | 2-(6-sulfonato-sodium-benzothiazolyl) | 3-methyl-4-(sulfonato-sodium)phenyl | 3-methyl-4-(sulfonato-sodium)phenyl |
| 6-2 | 2-benzothiazolyl | 4-(sulfonato-sodium)phenyl | 4-(sulfonato-sodium)phenyl |
| 6-3 | 2-(5-nitrobenzothiazolyl) | 2,4,5-trimethyl-3-(sulfonato-potassium)phenyl | 2,4,5-trimethyl-3-(sulfonato-potassium)phenyl |
| 6-4 | 2-(6-sulfonato-potassium-benzothiazolyl) | 2,3,5,6-tetramethyl-4-(sulfonato-potassium)phenyl | 2,3,5,6-tetramethyl-4-(sulfonato-potassium)phenyl |

TABLE 7-continued
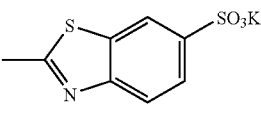
| Dye | $R_1$ | $R_2$ | $R_3$ |
|---|---|---|---|
| 6-5 | 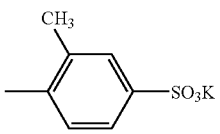 | 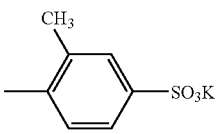 | 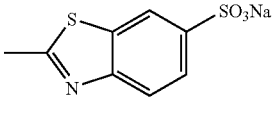 |
| 6-6 | 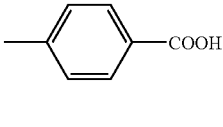 | 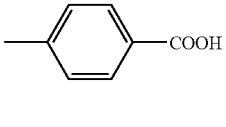 | 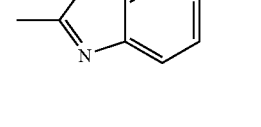 |
| 6-7 | 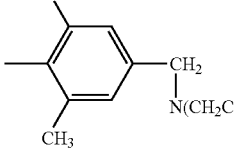 | 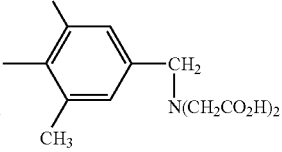 | 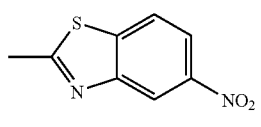 |
| 6-8 | 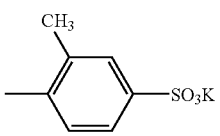 | 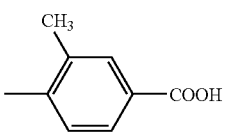 | 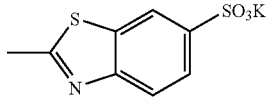 |
TABLE 8
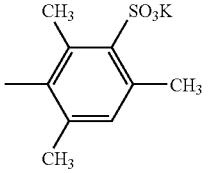
| Dye | $R_1$ | $R_2$ | $R_3$ | $R_4$ |
|---|---|---|---|---|
| 7-1 | 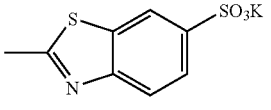 | 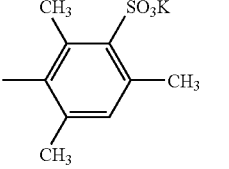 | | |

TABLE 8-continued
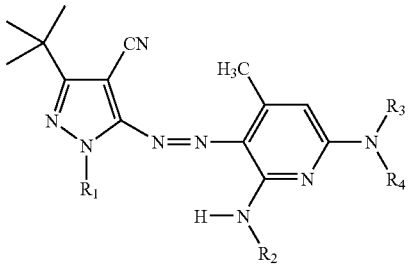
| Dye | R₁ | R₂ | R₃ | R₄ |
|---|---|---|---|---|
| 7-2 | 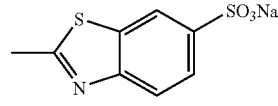 | 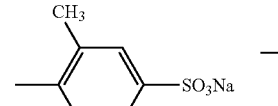 | 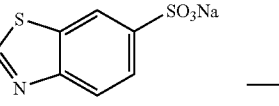 | 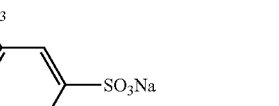 |
| 7-3 | 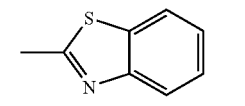 | 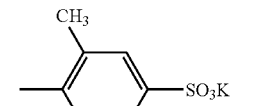 | 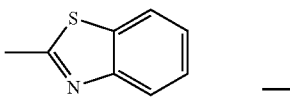 | 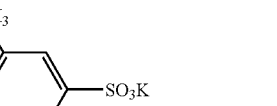 |
| 7-4 | 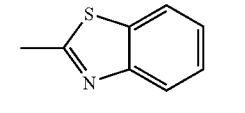 | 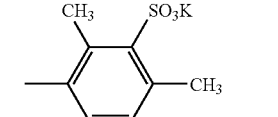 | 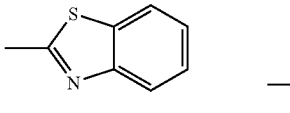 | 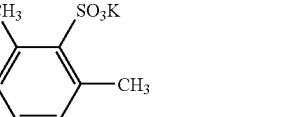 |
| 7-5 | 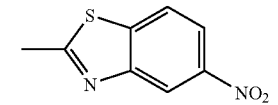 | 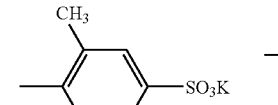 | 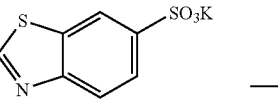 | 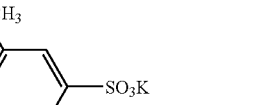 |
| 7-6 | 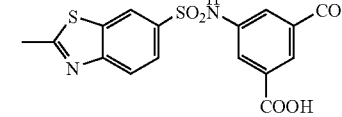 | 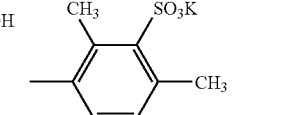 | 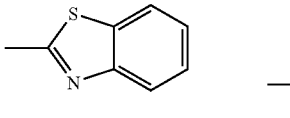 | 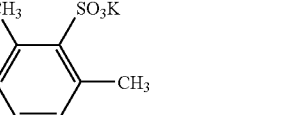 |
| 7-7 | 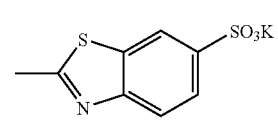 |  | 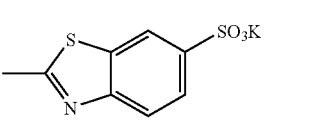 |  |
| 7-8 | 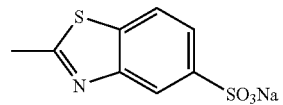 | 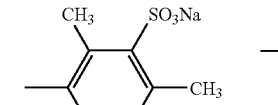 | 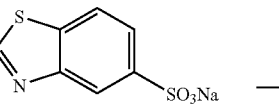 | 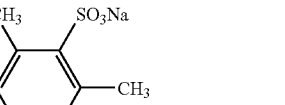 |

TABLE 8-continued
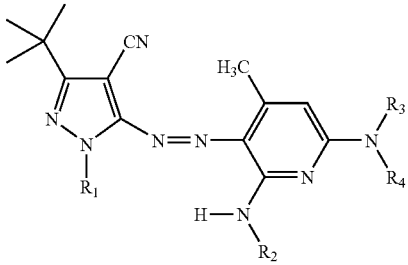
| Dye | R₁ | R₂ | R₃ | R₄ |
|---|---|---|---|---|
| 7-9 | 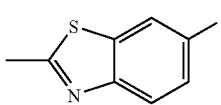 | 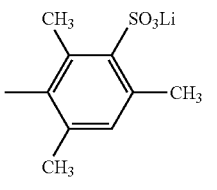 | 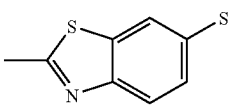 | 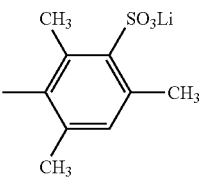 |
| 7-10 | 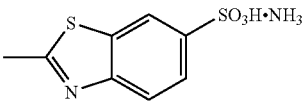 | 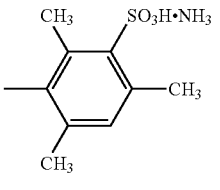 | 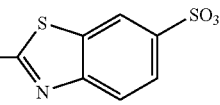 | 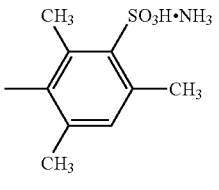 |
TABLE 9
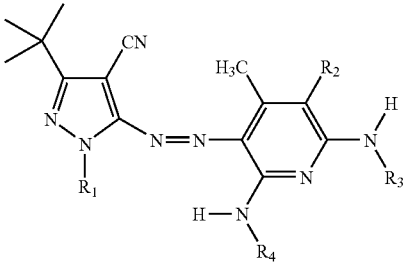
| Dye | R₁ | R₂ | R₃ | R₄ |
|---|---|---|---|---|
| 8-1 | 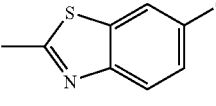 | H |  | 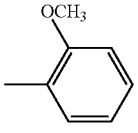 |
| 8-2 | 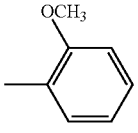 | H | 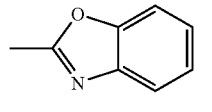 |  |
| 8-3 | 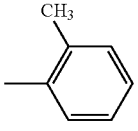 | CN | 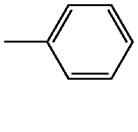 | 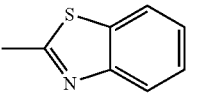 |

The azo dyes of the present invention are useful as image recording materials, particularly color image recording materials for ink jet recording, heat transfer recording, pressure-sensitive recording, electrophotography, transfer type silver halide photographic materials, printing inks, recording pens, and so forth. The azo dyes of the invention are particularly fit for use in ink jet recording materials, transfer type silver halide photographic materials, heat transfer recording materials, and electrophotographic recording materials. The most preferred application is ink jet recording. The dyes also find use in color filters for liquid crystal displays and solid-state image sensors, such as CCDs, and dye baths for textile.

The azo compounds of the invention can have selected substituents so as to exhibit physical properties desired for intended applications, such as solubility and thermal mobility. The azo compounds are used in a selected form suitable for intended applications, such as a solution or a dispersion (e.g., an emulsion or a suspension).

An ink-jet ink is prepared by dissolving and/or dispersing the azo compound of the invention in a lipophilic or an aqueous medium. Water-based ink using an aqueous medium is preferred. The ink composition of the invention can contain additives as needed, as long as the effects of the invention are not impaired. Useful additives include drying preventatives (wetting agents), anti-browning agents, emulsion stabilizers, penetrants, ultraviolet absorbers, antiseptics, antifungals, pH adjustors, surface tension modifiers, defoaming agents, viscosity modifiers, dispersants, dispersion stabilizers, rust preventatives, and chelating agents. These additives are directly added to a water-based ink formulation. Where an oil-soluble dye is used in the form of a dispersion, the additives are generally added to a prepared dye dispersion or, may be added to the oily phase or the aqueous phase in ink preparation.

Drying preventatives are preferably used for the purpose of preventing clogging of nozzles due to ink drying. Water-soluble organic solvents having a lower vapor pressure than water are preferred drying preventives. Examples of such water-soluble organic solvents include polyhydric alcohols, such as ethylene glycol, propylene glycol, diethylene glycol, polyethylene glycol, thiodiglycol, dithiodiglycol, 2-methyl-1,3-propanediol, 1,2,6-hexanetriol, acetylene glycol derivatives, glycerol, and trimethylolpropane; lower alkyl ethers of polyhydric alcohols, such as ethylene glycol monomethyl (or ethyl) ether, diethylene glycol monomethyl (or ethyl) ether, and triethylene glycol monoethyl (or butyl) ether; heterocyclic compounds, such as 2-pyrrolidone, N-methyl-2-pyrrolidone, 1,3-dimethyl-2-imidazolidinone, and N-ethylmorpholine; sulfur-containing compounds, such as sulfolane, dimethyl sulfoxide, and 3-sulfolene; polyfunctional compounds, such as diacetone alcohol and diethanolamine; and urea derivatives. Preferred of them are polyhydric alcohols, such as glycerol and diethylene glycol. These drying preventatives can be used either individually or as a combination of two or more thereof. A preferred content of the drying preventative in the ink composition is 10 to 50% by weight.

Penetrants are preferably added for the purpose of helping ink penetrate paper. Useful penetrants include alcohols, such as ethanol, isopropyl alcohol, butanol, di(or tri)ethylene glycol monobutyl ether, and 1,2-hexanediol; sodium lauryl sulfate, sodium oleate, and nonionic surface active agents. The content of the penetrant is decided so as not to cause feathering or strike-through. A penetrant content of 5 to 30% by weight in the ink composition will suffice to produce satisfactory effect.

UV absorbers are used to improve archival stability. Useful UV absorbers include benzotriazole compounds disclosed, e.g., in JP-A-58-185677, JP-A-61-190537, JP-A-2-782, JP-A-5-197075, and JP-A-9-34057, benzophenone compounds described, e.g., in JP-A-46-2784, JP-A-5-194483, and U.S. Pat. No. 3,214,463, cinnamic acid compounds described, e.g., in JP-B-48-30492, JP-B-56-21141, and JP-A-10-88106, triazine compounds disclosed, e.g., JP-A-4-298503, JP-A-8-53427, JP-A-8-239368, JP-A-10-182621, and JP-W-8-501291, and the compounds given in Research Disclosure No.24239. Compounds emitting fluorescence on UV absorption, i.e., fluorescent brightening agents, such as stilbene derivatives and benzoxazole derivatives, are also useful.

Anti-browning agents are used to improve archival stability. Various organic or metal complex anti-browning agents are usable. Organic anti-browning agents include hydroquinones, alkoxyphenols, dialkoxyphenols, phenols, anilines, amines, indanes, chromans, alkoxyanilines, and heterocyclic compounds. Metal complex anti-browning agents include nickel complexes and zinc complexes. Specific examples of the anti-browning agents are given in Research Disclosure, No. 17643, VII-I to VII-J,ibid, No. 15162,ibid, No. 18716, p. 650, left column,ibid, No. 36544, p. 527,ibid, No. 307105, p. 872, and the patents cited in ibid, No. 15162. The compounds represented by the general formulae and their specific examples described in JP-A-62-215272, pp. 127-137 are also useful.

Useful antifungals include sodium dehydroacetate, sodium benzoate, sodium pyridinethione-1-oxide, ethyl p-hydroxybenzoate, ad 1,2-benzisothiazolin-3-one and its salts. A preferred content of the antifungals in the ink composition ranges from 0.02 to 1.00% by weight.

The aforementioned neutralizing agents (organic bases and inorganic alkalis) serve as pH adjustors. For the purpose of improving ink storage stability, pH adjustors are preferably added to adjust the ink composition at a pH of 6 to 10, particularly 7 to 10, taking use in summer into consideration.

Surface tension modifiers include nonionic, cationic or anionic surface active agents. It is preferred for the ink-jet ink composition to have a surface tension of 20 to 60 mN/m, particularly 25 to 45 mN/m. It is preferred for the ink composition to have a viscosity of 30 mPa·s or less, particularly 20 mPa·s or less.

Useful anionic surface active agents include fatty acid salts, alkylsulfates, alkylbenzenesulfonates, alkylnaphthalenesulfonates, dialkylsufosuccinates, alkylphosphoric ester salts, naphthalenesulfonic acid-formalin condensates, and polyethylene glycol alkylsulfates. Useful nonionic surface active agents include polyethylene glycol alkyl ethers, polyethylene glycol alkyl allyl ethers, polyethylene glycol fatty acid esters, sorbitan fatty acid esters, polyoxyethylene sorbitan fatty acid esters, polyoxyethylene alkylamines, glycerol fatty acid esters, ethylene oxide/propylene oxide block copolymers, and acetylenic diol-based surfactants available from Air Products & Chemicals, Inc. under the trade name Surfynol. Amine oxide type amphoteric surface active agents, such as N,N-dimethyl-N-alkylamine oxides, are useful as well. The surface active agents described in JP-A-59-157636, pp. 37-38 and *Research Disclosure*, No. 308119 (1989) are also useful.

Antifoaming agents which can be added if desired include fluorine-containing compounds, silicone compounds, and chelating agents, such as EDTA.

Where the azo dye of the invention is dispersed in an aqueous medium, techniques that are preferably taken are described in JP-A-11-286637 and Japanese Patent Application Nos. 2000-78491, 2000-80259, and 2000-62370, in which coloring particles comprising a dye and an oil-soluble polymer are dispersed in an aqueous medium, or Japanese Patent Application Nos. 2000-78454, 2000-78491, 2000-203856, and 2000-203857, in which a dye dissolved in a high-boiling organic solvent is dispersed in an aqueous medium. The particulars of the methods for dispersing the dye in an aqueous medium and the kinds and amounts of the materials used therefore (oil-soluble polymers, high-boiling organic solvents, and additives) are selected appropriately with reference to the publications cited above. It is also possible to finely disperse the azo dye directly in an aqueous medium. Dispersants or surface active agents can help dispersing. Suitable dispersing apparatus include simple stirrers, impeller stirrers, in-line stirrers, mills (e.g., a colloid mill, a ball mill, a sand mill, an attritor, a roll mill or an agitator mill), ultrasonic stirrers, and high-pressure emulsifiers or homogenizers (e.g., Gaulin Homogenizer, Microfluidizer, and DeBEE2000).

In addition to the aforementioned literature, JP-A-5-148436, JP-A-5-295312, JP-A-7-97541, JP-A-7-82515, JP-A-7-118584, JP-A-11-286637, and Japanese Patent Application No. 2000-87539 furnish information about ink-jet ink formulations which are applicable to the present invention.

The aqueous medium which can be used in the ink composition of the present invention is water generally containing a water-miscible organic solvent. Useful water-miscible organic solvents include alcohols, e.g., methanol, ethanol, propanol, isopropyl alcohol, butanol, isobutanol, sec-butanol, t-butanol, pentanol, hexanol, cyclohexanol, and benzyl alcohol; polyhydric alcohols, e.g., ethylene glycol, diethylene glycol, triethylene glycol, polyethylene glycol, propylene glycol, dipropylene glycol, polypropylene glycol, butylene glycol, hexanediol, pentanediol, glycerol, hexanetriol, and thiodiglycol; glycol derivatives, e.g., ethylene glycol monomethyl ether, ethylene glycol monoethyl ether, ethylene glycol monobutyl ether, diethylene glycol monomethyl ether, diethylene glycol monobutyl ether, propylene glycol monomethyl ether, propylene glycol monobutyl ether, dipropylene glycol monomethyl ether, ethylene glycol diacetate, ethylene glycol monomethyl ether acetate, triethylene glycol monomethyl ether, triethylene glycol monoethyl ether, and ethylene glycol monophenyl ether; amines, e.g., ethanolamine, diethanolamine, triethanolamine, N-methyldiethanolamine, N-ethyldiethanolamine, morpholine, N-ethylmorpholine, ethylenediamine, diethylenetriamine, triethylenetetramine, polyethylene-imine, and tetramethylpropylenediamine; and other polar solvents, e.g., formamide, N,N-dimethylformamide, N,N-dimethylacetamide, dimethyl sulfoxide, sulfolane, 2-pyrrolidone, N-methyl-2-pyrrolidone, N-vinyl-2-pyrrolidone, 2-oxazolidone, 1,3-dimethyl-2-imidazolidinone, acetonitrile, and acetone. These solvents may be used either individually or as a combination of two or more thereof.

The ink-jet ink composition preferably contains the azo compound of the invention in a concentration of 0.2 to 10% by weight. The ink composition may contain known colorants in addition to the azo compound. In this case, it is preferred that a total concentration of colorants be within in the above range.

The ink-jet ink composition of the invention is used to form not only monochromatic but full color images. For full color images, magenta ink, cyan ink, and yellow ink are used. Black ink may be used in combination for tone adjustment.

Yellow dyes to be used in combination are arbitrarily chosen. Useful yellow dyes include aryl or heterylazo dyes having, as a coupling component, phenols, naphthols, anilines, heterocyclic compounds (e.g., pyrazolone or pyridone), open-chain active methylene compounds, etc.; azomethine dyes having an open-chain active methylene compound as a coupling component; methine dyes such as benzylidene dyes and monomethine oxonol dyes; quinone dyes such as naphthoquinone dyes and anthraquinone dyes; quinophthalone dyes, nitro dyes, nitroso dyes, acridine dyes, and acridinone dyes.

Cyan dyes to be used in combination are arbitrary. Useful cyan dyes include aryl or heterylazo dyes having phenols, naphthols, anilines, etc. as a coupling component; azomethine dyes having phenols, naphthols, heterocyclic compounds (e.g., pyrrolotriazole), etc. as a coupling component; polymethine dyes such as cyanine dyes, oxonol dyes, and merocyanine dyes; carbonium dyes such as diphenylmethane dyes, triphenylmethane dyes, and xanthene dyes; phthalocyanine dyes; anthraquinone dyes; indigo dyes; and thioindigo dyes.

Yellow or cyan dyes which do not develop a color until part of their chromophore is dissociated are also useful. Counter cations in this type of dyes include inorganic cations such as alkali metals or ammonium, organic cations such as pyridinium or a quaternary ammonium salt, or a polymeric cation having such a cation as a partial structure.

Black dyes which can be used in combination include disazo dyes, trisazo dyes, tetraazo dyes, and a carbon black dispersion.

Ink jet recording is carried out by supplying energy to ink-jet ink to form fine ink droplets which fly onto a known image-receiving medium to form an image. Known media include plain paper, resin-coated paper (for example, ink-jet papers disclosed in JP-A-8-169172, JP-A-8-27693, JP-A-2-276670, JP-A-7-276789, JP-A-9-323475, JP-A-62-238783, JP-A-10-153989, JP-A-10-217473, JP-A-10-235995, JP-A-10-337947, JP-A-10-217597, and JP-A-10-337947), films, electrophotographic papers, cloth, glass, metal, and earthenware.

Polymer latex compounds may be used for image formation to impart gloss, water resistance or improved weatherability to images. A latex compound is supplied to an image-receiving medium before, after or simultaneously with image formation. In other words, a latex compound may be present in either the medium or the ink composition or be separately applied in the form of liquid. For further details, reference can be made to Japanese Patent Application Nos. 2000-363090, 2000-315231, 2000-354380, 2000-343944, 2000-268952, 2000-299465, and 2000-297365.

Recording paper and recording film which can be used as a medium to be ink-jet printed with the ink of the invention usually comprise a substrate and an ink-receiving layer, and, if desired, a backcoating layer. The substrate includes paper, synthetic paper, and plastic films. Paper as a substrate is prepared from a slurry of chemical pulp (e.g., LBKP or NBKP), mechanical pulp (e.g., groundwood pulp (GP), pressurized groundwood pulp (PGW), refiner mechanical pulp (RMP), thermo-mechanical pulp (TMP), chemothermo-mechanical pulp (CTMP), chemomechanical pulp (CMP) or chemogroundwood pulp (CGP)) or used paper pulp (e.g., de-inked pulp (DIP)) which can contain, if desired, known additives such as pigments, binders, sizes, fixatives, cationic agents, paper strengthening agents, and the like by papermaking techniques with a wire paper machine, a cylinder paper machine, etc. The substrate preferably has a thickness of 10 to 250 μm and a basis weight of 10 to 250 g/m$_2$.

An ink-receiving layer or a backcoating layer is provided on the substrate either directly or after sizing with starch, polyvinyl alcohol, etc. or forming an anchor coat. If necessary, the substrate is smoothened on a machine calender, a temperature-gradient calender, a soft nip calender, etc. Preferred substrates are paper laminated on both sides with film of a polyolefin (e.g., polyethylene), polystyrene, polyethylene terephthalate, polybutene or a copolymer thereof and plastic films. It is desirable to add into the laminating resin a white pigment (e.g., titanium dioxide or zinc oxide) or a tinting material (e.g., cobalt blue, ultramarine or neodymium oxide).

The ink-receiving layer provided on the substrate comprises a pigment, preferably a white pigment, and an aqueous binder. Useful white pigments include inorganic ones, such as calcium carbonate, kaolin, talc, clay, diatomaceous earth, synthetic amorphous silica, aluminum silicate, magnesium silicate, calcium silicate, aluminum hydroxide, alumina, lithopone, zeolite, barium sulfate, calcium sulfate, titanium dioxide, zinc sulfide, and zinc carbonate; and organic ones, such as styrene plastic pigments, acrylic plastic pigments, urea resins, and melamine resins. Porous inorganic pigments are preferred. Those with a large surface area, such as synthetic amorphous silica, are more preferred. Silicic acid anhydride obtained by a dry process and hydrous silicic acid obtained by a wet process are both usable. Hydrous silicic acid is particularly preferred.

Useful aqueous binders include water-soluble polymers such as polyvinyl alcohol, silanol-modified polyvinyl alcohol, starch, cationic starch, casein, gelatin, carboxymethyl cellulose, hydroxyethyl cellulose, polyvinylpyrrolidone, polyalkylene oxides, and polyalkylene oxide derivatives; and water-dispersible polymers such as styrene-butadiene latices and acrylic emulsions. The aqueous binders are used either individually or as a combination thereof. Preferred of the recited binders are polyvinyl alcohol and silanol-modified polyvinyl alcohol for their adhesion to pigments and capability of forming a peel-resistant coat.

The ink-receiving layer can contain, in addition to the pigments and aqueous binders, mordants, waterproofing agents, light fastness improving agents, surface active agents, and other additives.

The mordant to be added to the ink-receiving layer is preferably immobilized. For this, polymeric mordants are preferably used. The details of useful polymeric mordants are given in JP-A-48-28325, JP-A-54-74430, JP-A-54-124726, JP-A-55-22766, JP-A-55-142339, JP-A-60-23850, JP-A-60-23851, JP-A-60-23852, JP-A-60-23853, JP-A-60-57836, JP-A-60-60643, JP-A-60-118834, JP-A-60-122940, JP-A-60-122941, JP-A-60-122942, JP-A-60-235134, JP-A-1-161236, and U.S. Pat. Nos. 2,484,430, 2,548,564, 3,148,061, 3,309,690, 4,115,124, 4,124,386, 4,193,800, 4,273,853, 4,282,305, and 4,450,224. In particular, the polymeric mordants described in JP-A-1-161236, pp.212-215 are preferred for obtaining images of high image quality with improved light fastness.

The waterproofing agents, which are effective for making images water-resistant, preferably include cationic resins, such as polyamide-polyamine epichlorohydrin, polyethylene-imine, polyamine sulfone, dimethyldiallylammonium chloride polymers, cationic polyacrylamide, and colloidal silica. Polyamide-polyamine epichlorohydrin is particularly preferred. A preferred cationic resin content in the image-receiving layer is 1 to 15% by weight, particularly 3 to 10% by weight.

The light fastness improving agents include zinc sulfate, zinc oxide, hindered amine antioxidants, and benzophenone or benzotriazole UV absorbers. Zinc sulfate is particularly suitable.

The surface active agents in the image-receiving layer function as a coating aid, a peel resistance improving agent, a slip improving agent or an antistatic agent. Useful surface active agents are described in JP-A-62-173463 and JP-A-62-183457. Organic fluorine compounds may be used in place of the surface active agents. Hydrophobic organic fluorine compounds, such as fluorine surface active agents, oily fluorine compounds (e.g., fluorine oil), and solid fluorine compounds (e.g., tetrafluoroethylene resin), are preferred. Details of the organic fluorine compounds are described in JP-B-57-9053 (cols. 8-17), JP-A-61-20994 and JP-A-62-135826. Other additives that can be added to the ink-receiving layer include pigment dispersants, thickeners, defoaming agents, dyes, fluorescent whitening agents, antiseptics, pH adjustors, matting agents, and hardeners. The ink-receiving layer can have a single or double layer structure.

The backcoating layer, which can be provided if desired, comprises a white pigment, an aqueous binder, and additives. The white pigment includes inorganic ones such as light precipitated calcium carbonate, heavy calcium carbonate, kaolin, talc, calcium sulfate, barium sulfate, titanium dioxide, zinc oxide, zinc sulfide, zinc carbonate, satin white, aluminum silicate, diatomaceous earth, calcium silicate, magnesium silicate, synthetic amorphous silica, colloidal silica, colloidal alumina, pseudoboehmite, aluminum hydroxide, alumina, lithopone, zeolite, hydrated halloysite, magnesium carbonate, and magnesium hydroxide; and organic ones such as styrene plastic pigments, acrylic plastic pigments, polyethylene, hollow particles, urea resins, and melamine resins.

Aqueous binders which can be used in the backcoating layer include water-soluble polymers such as styrene/maleic acid salt copolymers, styrene/acrylic acid salt copolymers, polyvinyl alcohol, silanol-modified polyvinyl alcohol, starch, cationic starch, casein, gelatin, carboxymethyl cellulose, hydroxyethyl cellulose, and polyvinylpyrrolidone; and water-dispersible polymers such as styrene-butadiene latices and acrylic emulsions. Additives which can be used in the backcoating layer include defoaming agents, foam-suppressors, dyes, fluorescent whitening agents, antiseptics, and waterproofing agents.

A polymer latex may be incorporated into any layer constituting the paper or film for ink-jet recording inclusive of the backcoating layer for the purpose of improving film properties, for example, dimensional stabilization, curling prevention, anti-blocking, and crack prevention. For further details, reference can be made to JP-A-62-245258, JP-A-62-136648, and JP-A-62-110066. Addition of a polymer latex having a low glass transition temperature (40° C. or lower) into a layer containing a mordant will prevent cracking or curling. Addition of a polymer latex having a high glass transition temperature to a backcoating layer is also effective for curling prevention.

The ink composition according to the present invention is applicable to any known ink jet recording systems, such as an electrostatic system in which ink droplets are ejected by an electrostatic attracting force, a piezoelectric system in which vibrating pressure by a piezoelectric element is utilized (pressure pulse system), an acoustic system in which electrical signals are converted to an acoustic beam, which is applied to ink, and ink is ejected by making use of a radiating pressure, and a thermal system in which air bubbles are generated by heat to eject ink droplets. Further, ink jet recording includes a system in which a number of fine droplets of low concentration ink called photoink are ejected, a system in which a plurality of ink formulations having substantially the same hue but different concentrations are used to improve image quality, and a system of using colorless transparent ink.

The Second Aspect of the Invention

In formula (2-I), $A_1$ represents —$CR_1$= or a nitrogen atom and $A_2$ represents —$CR_2$= or a nitrogen atom provided that $A_1$ and $A_2$ do not simultaneously represent a nitrogen atom. $A_1$ and $A_2$ preferably represent —$CR_1$= or —$CR_2$= respectively.

At least one of $R_6$ and $R_7$ represents an aromatic group or a heterocyclic group with the other representing a hydrogen atom, an aliphatic group, an aromatic group, a heterocyclic group, an acyl group, an alkoxycarbonyl group, an aryloxycarbonyl group or a sulfamoyl group, wherein each group may have a substituent. It is preferred that at least one of $R_6$ and $R_7$ be an aromatic group or a heterocyclic group, with the other being a hydrogen atom, an aromatic group, a heterocyclic group, an acyl group, an alkylsulfonyl group or an arylsulfonyl group. It is more preferred that at least one of $R_6$ and $R_7$ be an aromatic group or a heterocyclic group, with the other being a hydrogen atom, an aromatic group, a heterocyclic group, an acyl group or an arylsulfonyl group. It is particularly preferred that at least one of $R_6$ and $R_7$ be an aromatic group or a heterocyclic group, with the other being a hydrogen atom, an aromatic group or a heterocyclic group. Each of these groups may have a substituent.

The aromatic group or the heterocyclic group as $R_6$ and/or $R_7$ is preferably such a group as has a substituent or a lone electron pair on at least one, preferably both, of the atoms adjacent to the carbon atom bonded to the nitrogen atom of the amino group.

G, $R_1$, and $R_2$ each represent a hydrogen atom, a halogen atom, an aliphatic group, an aromatic group, a heterocyclic group, a cyano group, a carboxyl group, a carbamoyl group, an alkoxycarbonyl group, an aryloxycarbonyl group, an acyl group, a hydroxyl group, an alkoxy group, an aryloxy group, a silyloxy group, an acyloxy group, a carbamoyloxy group, a heterocyclic oxy group, an alkoxycarbonyloxy group, an aryloxycarbonyloxy group, an amino group substituted with an alkyl group, an aromatic group or a heterocyclic group, an acylamino group, a ureido group, a sulfamoylamino group, an alkoxycarbonylamino group, an aryloxycarbonylamino group, an alkylsulfonylamino group, an arylsulfonylamino group, a nitro group, an alkylthio group, an arylthio group, a heterocyclic thio group, an alkylsulfonyl group, an arylsulfonyl group, an alkylsulfinyl group, an arylsulfinyl group, a sulfamoyl group or a sulfo group, wherein each group may have a substituent, with proviso that G is not an alkyl-substituted amino group when $A_1$ and $A_2$ represent —$CR_1$= and —$CR_2$= respectively.

$R_1$ and $R_6$ may be taken together, or $R_6$ and $R_7$ may be taken together, each to form a 5- or 6-membered ring.

G preferably represents a hydrogen atom, a halogen atom, an aliphatic group, an aromatic group, a hydroxyl group, an alkoxy group, an aryloxy group, an acyloxy group, a heterocyclic oxy group, an amino group substituted with an alkyl group, an aromatic group or a heterocyclic group, an acylamino group, a ureido group, a sulfamoylamino group, an alkoxycarbonylamino group, an aryloxycarbonylamino group, an alkylthio group, an arylthio group or a heterocyclic thio group. G more preferably represents a hydrogen atom, a halogen atom, an alkyl group, a hydroxyl group, an alkoxy group, an aryloxy group, an acyloxy group, an amino group substituted with an aromatic group or a heterocyclic group or an acylamino group. Particularly preferably G represents a hydrogen atom, an amino group substituted with an aromatic group or a heterocyclic group or an acylamino group.

$R_1$ and $R_2$ each preferably represent a hydrogen atom, an alkyl group, an alkoxycarbonyl group, a carboxyl group, a carbamoyl group or a cyano group. Each of these groups may have a substituent.

The substituents possessed by $R_1$, $R_2$, $R_6$, $R_7$ or G include the atoms (except a hydrogen atom) and the groups recited above as $R_1$ and $R_2$.

Where an azo compound formed by coupling reaction between the compound of formula (2-I) and a diazonium salt is a water-soluble dye, it is preferred for any one of $R_1$, $R_2$, $R_6$, $R_7$, and G to have an ionic hydrophilic group as a substituent. Suitable ionic hydrophilic groups include a sulfo group, a carboxyl group, and a quaternary ammonium group. A carboxyl group and a sulfo group are more preferred, with a sulfo group being particularly preferred. The carboxyl group or the sulfo group may be in a salt form. Suitable counter ions forming the salt include alkali metal ions (e.g., a sodium ion and a potassium ion) and organic cations (e.g., a tetramethylguanidium ion).

The substituents represented by G, $R_1$, and $R_2$ will be described in more detail. The term "halogen atom" includes a fluorine atom, a chlorine atom, and a bromine atom, with a fluorine atom and a chlorine atom being suitable.

The term "aliphatic group" includes a substituted or unsubstituted alkyl group, a substituted or unsubstituted alkenyl group, a substituted or unsubstituted alkynyl group, and a substituted or unsubstituted aralkyl group. The aliphatic group may have a branched structure or a cyclic structure. The aliphatic group preferably contains 1 to 20, particularly 1 to 16, carbon atoms. The aryl moiety of the aralkyl group is preferably a phenyl group or a naphthyl group, with a phenyl group being more preferred. Suitable examples of the aliphatic group are methyl, ethyl, butyl, isopropyl, t-butyl, hydroxyethyl, methoxyethyl, cyanoethyl, trifluoromethyl, 3-sulfopropyl, 4-sulfobutyl, cyclohexyl, benzyl, 2-phenethyl, vinyl, and allyl.

The term "aromatic group" is used to include a substituted or unsubstituted aromatic group. The aromatic group is preferably a phenyl group or a naphthyl group. A phenyl group is more preferred. The aromatic group preferably contains 6 to 20, particularly 6 to 16, carbon atoms. Suitable examples of the aromatic group are phenyl, p-tolyl, p-methoxyphenyl, o-chlorophenyl, m-(3-sulfopropylamino)phenyl, 2,6-diethylphenyl, 2,4,6-trimethylphenyl, 2,6-dimethyl-4-sulfophenyl, and 2,4-disulfophenyl.

Where one of $R_4$ and $R_5$ in formula (2-II) and/or one of $R_6$ and $R_7$ in formulae (2-I) and (2-II) is/are a hydrogen atom, the other or others represent an aromatic group or a heterocyclic group. The aromatic group represented by the other is preferably a phenyl group having a substituent at the o-position, such as o-chlorophenyl, o-(3-sulfopropylamino)phenyl, o-cyanophenyl, 2,6-diethylphenyl, 2,4,6-trimethylphenyl, 2,6-dimethyl-4-sulfophenyl or 2,4-disulfophenyl.

The term "heterocyclic group" as used herein includes a substituted and an unsubstituted heterocyclic group, which may have an aliphatic ring, an aromatic ring or a hetero ring condensed. The heterocyclic group is preferably 5- or 6-membered. Suitable substituents on the heterocyclic group include an aliphatic group, a halogen atom, an alkylsulfonyl group, an arylsulfonyl group, an acyl group, an acylamino group, a sulfamoyl group, a carbamoyl group, and an ionic hydrophilic group. Suitable examples of the heterocyclic group are 2-pyridyl, 2-thienyl, 2-thiazolyl, 2-benzothiazolyl, 2-benzoxazolyl, and 2-furyl.

Where one of $R_4$ and $R_5$ in formula (2-II) and/or one of $R_6$ and $R_7$ in formulae (2-I) and (2-II) is/are a hydrogen atom, the heterocyclic group represented by the other is preferably 2-pyridyl, 2-thienyl, 2-thiazolyl, 2-benzothiazolyl, 2-benzoxazolyl, 2-imidazolyl or 2-indolenyl.

The term "carbamoyl group" includes a substituted and an unsubstituted carbamoyl group. Suitable substituents on a carbamoyl group include an alkyl group. Suitable examples of the carbamoyl group are methylcarbamoyl and dimethylcarbamoyl.

The term "alkoxycarbonyl group" means a substituted or unsubstituted alkoxycarbonyl group. The alkoxycarbonyl group preferably contains 2 to 12 carbon atoms as unsubstituted. An ionic hydrophilic group is a suitable substituent. An ethoxycarbonyl group is a suitable alkoxycarbonyl group.

The term "aryloxycarbonyl group" means a substituted or unsubstituted aryloxycarbonyl group. An aryloxycarbonyl group having 7 to 12 carbon atoms as unsubstituted is preferred. Suitable substituents on the aryloxycarbonyl group include an ionic hydrophilic group. A phenoxycarbonyl group is a suitable example of the aryloxycarbonyl group.

The term "acyl group" includes a substituted acyl group and an unsubstituted acyl group. An acyl group having 1 to 12 carbon atoms as unsubstituted is suitable. An ionic hydrophilic group is a suitable substituent. Suitable examples of the acyl group include acetyl and benzoyl.

The term "alkoxy group" includes a substituted alkoxy group and an unsubstituted alkoxy group. An alkoxy group containing 1 to 12 carbon atoms as unsubstituted is suitable. Suitable substituents on an alkoxy group include an alkoxy group, a hydroxyl group, and an ionic hydrophilic group. Examples of suitable alkoxy groups are methoxy, ethoxy, isopropoxy, methoxyethoxy, hydroxyethoxy, and 3-carboxypropoxy.

The term "aryloxy group" means a substituted or unsubstituted aryloxy group. An aryloxy group containing 6 to 12 carbon atoms as unsubstituted is preferred. Suitable substituents on the aryloxy group include an alkoxy group and an ionic hydrophilic group. Examples of suitable alkoxy groups are phenoxy, p-methoxyphenoxy, and o-methoxyphenoxy.

The term "acyloxy group" means a substituted or unsubstituted acyloxy group. An acyloxy group having 1 to 12 carbon atoms as unsubstituted is preferred. Suitable substituents for the acyloxy group include an ionic hydrophilic group. Suitable examples of the acyloxy group are acetoxy and benzoyloxy.

The term "carbamoyloxy group" means a substituted or unsubstituted carbamoyloxy group. Suitable substituents on the carbamoyloxy group include an alkyl group. Suitable carbamoyloxy groups include an N-methylcarbamoyloxy group.

The term "heterocyclic oxy group" means a substituted or unsubstituted heterocyclic oxy group. A heterocyclic oxy group having 1 to 9 carbon atoms as unsubstituted is preferred. Suitable substituents on the heterocyclic oxy group include an alkyl group and a halogen atom. The heterocyclic oxy group suitably includes a 2-pyridyloxy group.

The term "alkoxycarbonyloxy group" denotes a substituted or unsubstituted alkoxycarbonyloxy group. An alkoxycarbonyloxy group having 2 to 10 carbon atoms as unsubstituted is preferred. Substituents on the alkoxycarbonyloxy group preferably include an alkyl group. The alkoxycarbonyloxy group preferably includes an ethoxycarbonyloxy group.

The term "aryloxycarbonyloxy group" denotes a substituted or unsubstituted aryloxycarbonyloxy group. An aryloxycarbonyloxy group preferably contains 6 to 16 carbon atoms as unsubstituted. Suitable substituents on the aryloxycarbonyloxy group are an alkyl group and a halogen atom. Suitable aryloxycarbonyloxy groups include a 2-ethylphenoxycarbonyloxy group.

The language "amino group substituted with an alkyl group, an aromatic group or a heterocyclic group" excludes an unsubstituted amino group. The alkyl group, the aromatic group or the heterocyclic group may further have a substituent.

The term "alkylamino group" means a substituted or unsubstituted alkylamino group. An alkylamino group having 1 to 6 carbon atoms as unsubstituted is preferred. An ionic hydrophilic group is a suitable substituent. Suitable examples of the alkylamino group are methylamino and diethylamino.

The term "arylamino group" indicates a substituted or unsubstituted arylamino group. An arylamino group having 6 to 12 carbon atoms as unsubstituted is preferred. Suitable substituents on the arylamino group include a halogen atom and an ionic hydrophilic group. Suitable arylamino groups are anilino and 2-chloroanilino.

The term "acylamino group" denotes a substituted or unsubstituted acylamino group. An acylamino group containing 2 to 12 carbon atoms as unsubstituted is preferred. An ionic hydrophilic group is a suitable example of the substituents on the acylamino group. Suitable acylamino groups include acetylamino, propionylamino, benzoylamino, N-phenylacetylamino, and 3,5-disulfobenzoylamino.

The term "ureido group" means a substituted or unsubstituted ureido group. A ureido group containing 1 to 12 carbon atoms as unsubstituted is preferred. Suitable substituents for the ureido group include an alkyl group and an aromatic group. Suitable examples of the ureido group are 3-methylureido, 3,3-dimethylureido, and 3-phenylureido.

The term "sulfamoylamino group" denotes a substituted or unsubstituted sulfamoylamino group. Suitable substituents for the sulfamoylamino group include an alkyl group. The sulfamoylamino group suitably includes an N,N-dipropylsulfamoyl group.

The term "alkoxycarbonylamino group" means a substituted or unsubstituted alkoxycarbonylamino group. An alkoxycarbonylamino group having 2 to 12 carbon atoms as unsubstituted is preferred. An ionic hydrophilic group is a suitable substituent. The alkoxycarbonylamino group includes an ethoxycarbonylamino group.

The term "aryloxycarbonylamino group" includes a substituted or unsubstituted aryloxycarbonylamino group. An aryloxycarbonylamino group having 7 to 12 carbon atoms as unsubstituted is preferred. An ionic hydrophilic group is a preferred substituent. A phenoxycarbonylamino group is a suitable aryloxycarbonylamino group.

The term "alkylsulfonylamino group" and the term "arylsulfonylamino group" mean a substituted or unsubstituted alkylsulfonylamino group and a substituted or unsubstituted arylsulfonylamino group, respectively. Those containing 1 to 12 carbon atoms as unsubstituted are preferred. Suitable substituents for the alkyl- or arylsulfonylamino group include ionic hydrophilic groups. Suitable examples of the alkyl- or arylsulfonylamino groups include methanesulfonylamino, N-phenylmethanesulfonylamino, benzenesulfonylamino, and 3-carboxybenzenesulfonylamino.

The terms "alkylthio group", "arylthio group", and "heterocyclic thio group" denote a substituted or unsubstituted alkylthio group, a substituted or unsubstituted arylthio group, and a substituted or unsubstituted heterocyclic thio group, respectively. Those containing 1 to 12 carbon atoms as unsubstituted are preferred. Suitable substituents on these groups include ionic hydrophilic groups. Examples of these groups include methylthio and 2-pyridylthio.

The terms "alkylsulfonyl group" and "arylsulfonyl group" mean a substituted or unsubstituted alkylsulfonyl group and a substituted or unsubstituted arylsulfonyl group, respectively. Those having 1 to 12 carbon atoms as unsubstituted are preferred. Suitable substituents on these group include an alkyl group and an ionic hydrophilic group. Suitable examples of these groups are a methanesulfonyl group and a 4-carboxybenzenesulfonyl group.

The terms "alkylsulfinyl group" and "arylsulfinyl group" denote a substituted or unsubstituted alkylsulfinyl group and a substituted or unsubstituted arylsulfinyl group, respectively. Those having 1 to 12 carbon atoms as unsubstituted are preferred. Suitable substituents on these group include an alkyl group and a phenyl group. Suitable examples of the alkylsulfinyl group and the arylsulfinyl group include methanesulfinyl and phenylsulfinyl.

The term "sulfamoyl group" means a substituted or unsubstituted sulfamoyl group. An alkyl group is a suitable substituent. The sulfamoyl group suitably includes dimethylsulfamoyl and di-(2-hydroxyethyl)sulfamoyl.

Of the compounds represented by formula (2-I) preferred are those represented by formula (2-II):

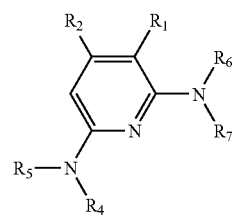

(2-II)

wherein $R_1$, $R_2$, $R_4$, $R_5$, $R_6$, and $R_7$ are as defined above.

It is preferred that one of $R_4$ and $R_5$ be an aromatic group or a heterocyclic group, with the other being a hydrogen atom, an aromatic group, a heterocyclic group, an acyl group, an alkylsulfonyl group or an arylsulfonyl group. It is more preferred that one of $R_4$ and $R_5$ be an aromatic group or a heterocyclic group, with the other being a hydrogen atom, an aromatic group or a heterocyclic group. The preference for the aromatic group and the heterocyclic group represented by $R_6$ or $R_7$ applies to those represented by $R_4$ or $R_5$.

The groups represented by $R_1$, $R_2$, $R_4$, $R_5$, $R_6$, and $R_7$ in formula (2-II) may each have a substituent. Suitable substituents therefore include those recited above as substituents G, $R_1$, and $R_2$ in formula (2-I) and ionic hydrophilic groups.

The compounds represented by formula (2-I) preferably have the following combinations of substituents.

(a) One of $R_6$ and $R_7$ represents an aromatic group or a heterocyclic group, with the other representing a hydrogen atom, an alkyl group, an aromatic group, a heterocyclic group, a sulfonyl group or an acyl group, preferably a hydrogen atom, an aromatic group, a heterocyclic group or a sulfonyl group, more preferably a hydrogen atom, an aromatic group or a heterocyclic group.

(b) G represents a hydrogen atom, a halogen atom, an alkyl group, a hydroxyl group, an amino group substituted with an aromatic group or a heterocyclic group or an acylamino group, preferably a hydrogen atom, a halogen atom, an amino group substituted with an aromatic group or a heterocyclic group or an acylamino group, more preferably a hydrogen atom, an amino group substituted with an aromatic group or a heterocyclic group or an acylamino group.

(c) $A_1$ represents —$CR_1$═ and $A_2$ represents —$CR_2$═, wherein $R_1$ and $R_2$ each represents a hydrogen atom, a halogen atom, a cyano group, a carbamoyl group, a carboxyl group, an alkyl group, a hydroxyl group or an alkoxy group, preferably a hydrogen atom, a cyano group, a carbamoyl group or an alkoxy group.

Of the compounds represented by formulae (2-I) and (2-II), those in which at least one of the substituents is selected from the above-recited preferred combinations of atoms or groups are preferred; those in which more substituents are selected from the respective preferred atoms or groups are more preferred; and those in which all the substituents are selected from the respective preferred atoms or groups are particularly preferred.

The process of producing an azo compound according to the present invention comprises coupling between the compound of formula (2-I), preferably the compound of formula (2-II), as a coupling component and a diazonium salt formed by a diazotizing agent. The resulting azo compound is suitable for use as a color or a dye.

Diazonium salts which can be used in the coupling reaction preferably include aromatic or heterocyclic compounds having an amino group. Heterocyclic compounds having an amino group are more preferred.

The diazotizing agent which can be used to form a diazonium salt includes a hydrochloric acid solution of sodium nitrite, isopentyl nitrite, and nitrosylsulfiric acid, with a hydrochloric acid solution of sodium nitrite being preferred.

In carrying out the coupling reaction, pyridine is a preferred solvent for the compounds of formulae (2-I) and (2-II).

Specific examples of the compounds represented by formulae (2-I) and (2-II) are shown in Tables 1 to 5 for illustrative purposes only but not for limitation.

TABLE 2-1

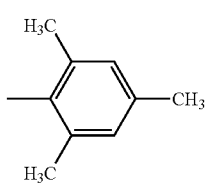

| Compound | $R_2$ | $R_4$ | $R_6$ | $R_7$ |
|---|---|---|---|---|
| 2-1-1 | —$CH_3$ | 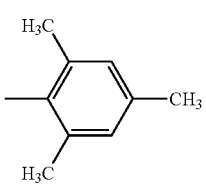 | 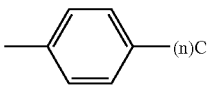 | —H |
| 2-1-2 | —$CH_3$ | 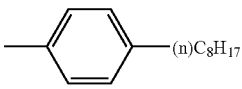 | 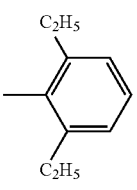 | —H |
| 2-1-3 | —$CH_3$ | 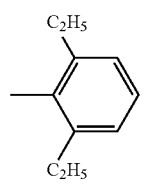 | 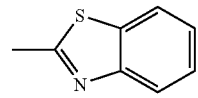 | 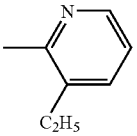 |
| 2-1-4 | —$CH_3$ | 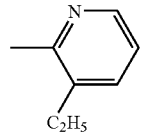 | 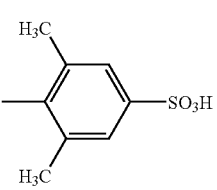 | —H |
| 2-1-5 | —$CH_2COOH$ | 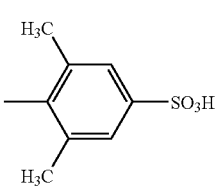 | 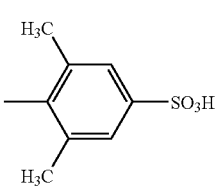 | —H |

TABLE 2-2

[Structure: pyridine with R2 at 4-position, CONH2 at 3-position, NH-R4 at 6-position, N(R6)(R7) at 2-position]

| Compound | R₂ | R₄ | R₆ | R₇ |
|---|---|---|---|---|
| 2-1-6 | —COOH | 2-methyl-4,6-disulfophenyl (SO₃H, HO₃S) | 2-methyl-4,6-disulfophenyl (SO₃H, HO₃S) | —H |
| 2-1-7 | —CH₂ | 2-methyl-6-(C₁₄H₂₇O)phenyl | 2-methyl-6-(C₁₄H₂₇O)phenyl | —H |
| 2-1-8 | —CH₃ | 2-methyl-6-t-C₄H₉-phenyl | 4-n-C₈H₁₇-phenyl | —H |
| 2-1-9 | —CH₃ | 2-methyl-3,5-dicarboxyphenyl (HOOC, COOH) | 2-methyl-4,6-disulfophenyl (HO₃S, SO₃H) | —H |
| 2-1-10 | —CH₃ | 2,4,6-trimethylphenyl (mesityl) | 2,6-dichlorophenyl | —H |

TABLE 2-3

[Structure: pyridine with R2 at 4-position, NH-R4 at 6-position, N(R6)(R7) at 2-position]

| Compound | R₂ | R₄ | R₆ | R₇ |
|---|---|---|---|---|
| 2-1-11 | —CH₃ | 2,4,6-trimethylphenyl (mesityl) | 2,4,6-trimethylphenyl (mesityl) | —H |

TABLE 2-3-continued
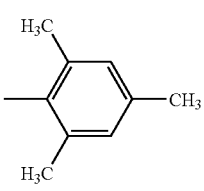
| Compound | R$_2$ | R$_4$ | R$_6$ | R$_7$ |
|---|---|---|---|---|
| 2-1-12 | —CH$_3$ | 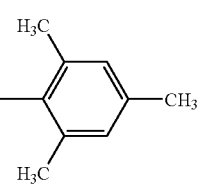 | 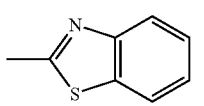 | 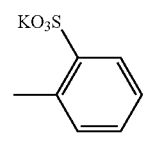 |
| 2-1-13 | —CH$_2$COOK | 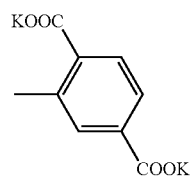 | 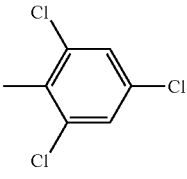 | —SO$_2$CH$_3$ |
| 2-1-14 | —CH$_3$ | 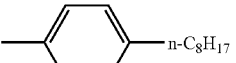 | 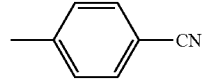 | 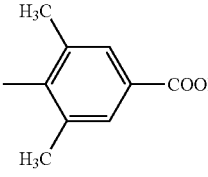 |
| 2-1-15 | —H | 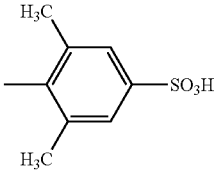 | 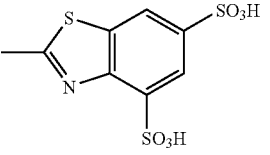 | 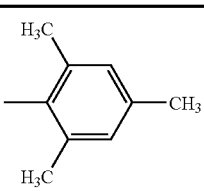 |
TABLE 2-4
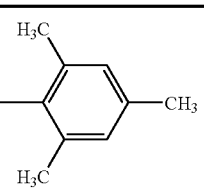
| Compound | R$_2$ | R$_4$ | R$_6$ | R$_7$ |
|---|---|---|---|---|
| 2-1-11 | —CH$_3$ | (3,4,5-trimethylphenyl) | (3,4,5-trimethylphenyl) | —H |

TABLE 2-4-continued
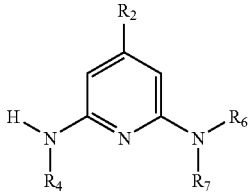
| Compound | R$_2$ | R$_4$ | R$_6$ | R$_7$ |
|---|---|---|---|---|
| 2-1-12 | —CH$_3$ | 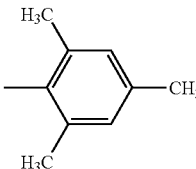 | 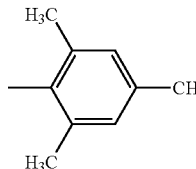 | 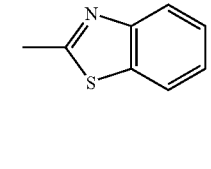 |
| 2-1-13 | —CH$_2$COOK | 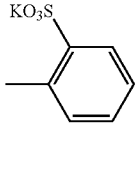 | 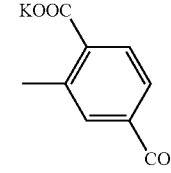 | —SO$_2$CH$_3$ |
| 2-1-14 | —CH$_3$ | 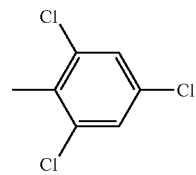 | 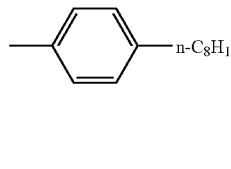 | 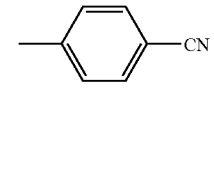 |
| 2-1-15 | —H | 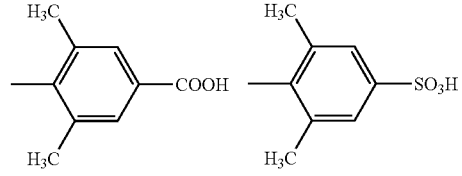 | 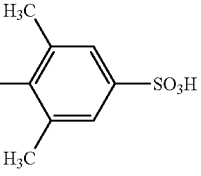 | 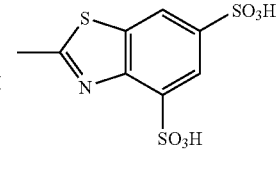 |
TABLE 2-5
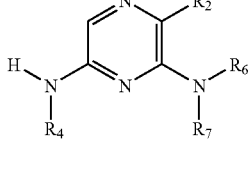
| Compound | R$_2$ | R$_4$ | R$_6$ | R$_7$ |
|---|---|---|---|---|
| 2-1-21 | —CH$_3$ | 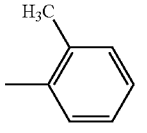 | 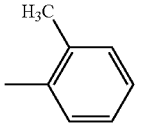 | —H |
| 2-1-22 | —H | 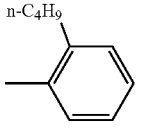 | 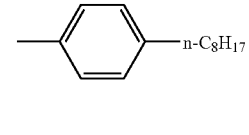 | —H |

TABLE 2-5-continued

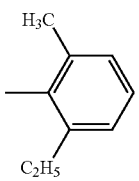

| Compound | R₂ | R₄ | R₆ | R₇ |
|---|---|---|---|---|
| 2-1-23 | —H | 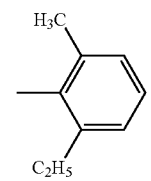 | 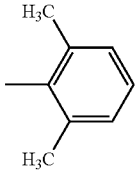 | —SO₂CH₃ |
| 2-1-24 | —Cl | 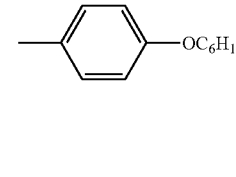 | 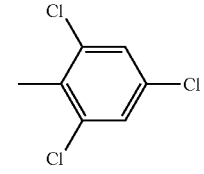 | 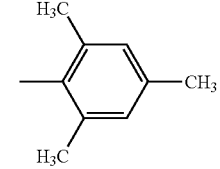 |
| 2-1-25 | —Cl | 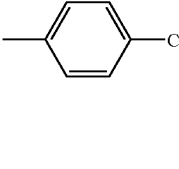 | 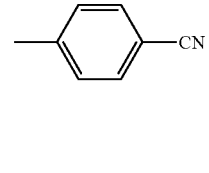 | |

EXAMPLES

The present invention will now be illustrated in greater detail with reference to Synthesis Examples and Examples, but it should be understood that the invention is not deemed to be limited thereto. Unless otherwise noted, all the percents and parts are by weight.

Synthesis Example 1

Synthesis of Compound 1-1

1) Synthesis of Compound 1-1a

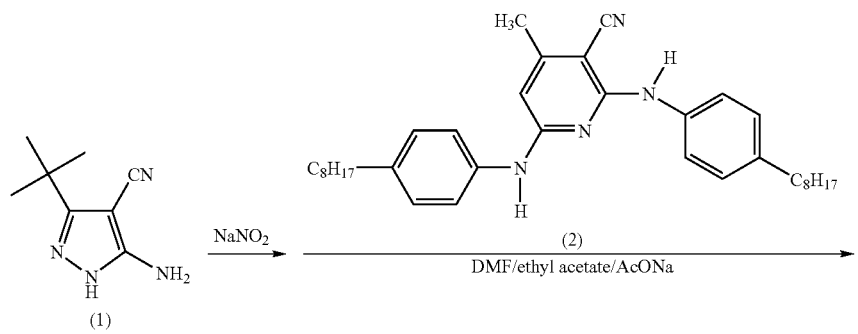

-continued

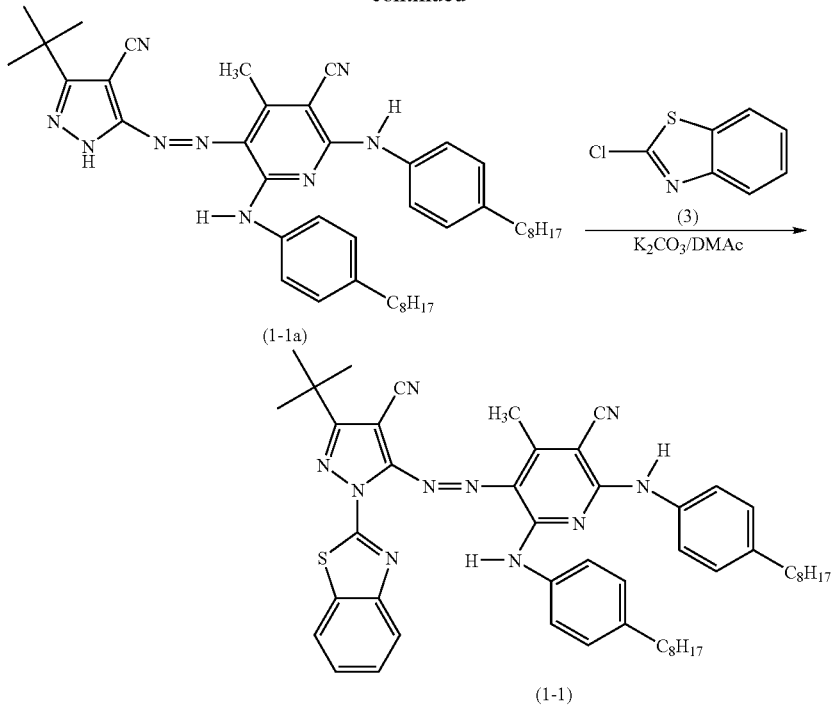

A mixture of 8 g (48.7 mmol) of 5-amino-3-t-butyl-4-cyanopyrazole (1), 15 ml of concentrated hydrochloric acid, and 50 ml of water was stirred at an inner temperature of 5° C., and 3.36 g (48.7 mmol) of sodium nitrite was added thereto in divided portions over 10 minutes. After the addition, the stirring was continued for 10 minutes to form a diazonium salt.

Separately, 21.3 g (40.6 mmol) of coupling component (2) was put in a three-necked flask, and 50 g of sodium acetate, 50 ml of dimethylformamide (DMF), and 50 ml of ethyl acetate were added thereto. The mixture was stirred and cooled to an inner temperature of 5° C. The diazonium salt was put into the mixture over 10 minutes, and the stirring was continued for an additional 30 minute period. Three hundred milliliters of a saturated aqueous solution of sodium chloride was added to the reaction mixture. The precipitate thus formed was collected by filtration by suction to isolate 24.2 g (85%) of compound 1-1a.

2) Synthesis of Compound 1-1

To 28.0 g (40 mmol) of compound 1-1a were added 8.8 g (52 mmol) of 2-chlorobenzothiazole (heterylating agent 3), 5.5 g of potassium carbonate, and 100 ml of dimethylacetamide (DMAc), and the mixture was heated at 100° C. for 1 hour. After completion of the reaction, the reaction mixture was cooled to room temperature, and 400 ml of a saturated aqueous solution of sodium chloride was added thereto. The precipitate thus formed was collected by suction filtration. Recrystallization from acetonitrile gave 33.3 g (80%) of compound 1-1.

$\lambda_{max}$=545 nm (DMF solution) m/z (positive ion mode)= 834

Compounds shown in Table 10 were synthesized in the same manner as in Synthesis Example 1. The results are also shown in Table 10.

TABLE 10

| Dye | Yield (%) | $\lambda_{max}$ (nm) in DMF |
|---|---|---|
| 1-2 | 75.2 | 548 |
| 1-3 | 68.3 | 547 |
| 1-4 | 82.5 | 550 |
| 1-5 | 81.1 | 540 |
| 1-6 | 80.5 | 551 |
| 1-7 | 88.7 | 549 |
| 1-8 | 72.3 | 555 |
| 1-9 | 66.9 | 545 |
| 1-10 | 68.3 | 553 |
| 1-11 | 53.8 | 556 |
| 1-12 | 61.2 | 560 |
| 1-13 | 63.3 | 548 |
| 1-14 | 67.3 | 547 |
| 1-15 | 71.1 | 561 |
| 1-16 | 61.3 | 559 |
| 1-17 | 68.2 | 558 |

Synthesis Example 2

Synthesis of Compound 2-1

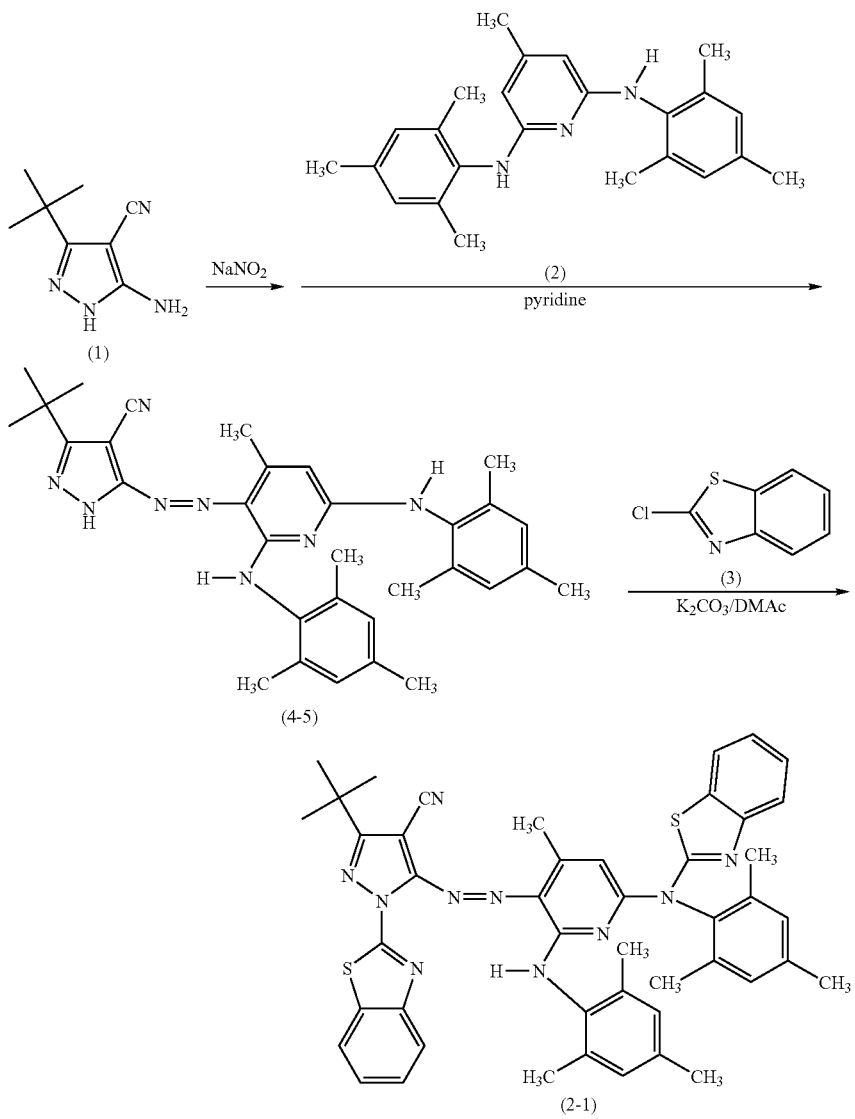

1) Synthesis of Compound 2-1a

A mixture of 8 g (48.7 mmol) of 5-amino-3-t-butyl-4-cyanopyrazole (1), 15 ml of concentrated hydrochloric acid, 8 ml of acetic acid, and 12 ml of propionic acid was stirred at an inner temperature of 5° C., and a solution of 3.36 g (48.7 mmol) of sodium nitrite in 10 ml of water was added thereto dropwise over 10 minutes. After the dropwise addition, the stirring was continued for 30 minutes to form a diazonium salt. Separately, 100 ml of pyridine was added to 18.5 g (40.6 mmol) of coupling component (2), and the mixture was stirred and cooled to an inner temperature of 5° C. The diazonium salt was put into the mixture over 30 minutes, and the stirring was continued for an additional 30 minute period. Three hundred milliliters of a saturated aqueous solution of sodium chloride was added to the reaction mixture. The precipitate was collected by filtration by suction to isolate compound (4-5) in a yield of 17.6 g (75%).

2) Synthesis of Compound 2-1

To 21.4 g (40 mmol) of compound (4-5) were added 17 g (100 mmol) of 2-chlorobenzothiazole (heterylating agent 3), 5.5 g of potassium carbonate, and 100 ml of DMAc, and the mixture was heated at 110° C. for 4 hours. After completion of the reaction, the reaction mixture was cooled to room temperature, and 400 ml of a saturated aqueous solution of sodium chloride was added thereto. The precipitate thus formed was collected by suction filtration. Recrystallization from acetonitrile yielded 15.4 g (48%) of compound 2-1.

$\lambda_{max}$=558 nm (DMF solution) m/z (positive ion mode)= 802

Compounds shown in Table 11 were synthesized in the same manner as in Synthesis Example 2. The results are also shown in the Table.
TABLE 11
| Dye | Yield (%) | $\lambda_{max}$ (nm) in DMF |
| --- | --- | --- |
| 2-2 | 71.3 | 543 |
| 2-3 | 68.2 | 541 |
| 2-4 | 65.4 | 558 |
| 2-5 | 60.3 | 555 |
| 2-6 | 58.3 | 560 |
| 2-7 | 57.3 | 560 |
| 2-8 | 62.3 | 557 |
| 2-9 | 61.1 | 558 |
TABLE 11-continued
| Dye | Yield (%) | $\lambda_{max}$ (nm) in DMF |
| --- | --- | --- |
| 2-10 | 55.5 | 563 |
| 2-11 | 63.3 | 560 |
| 2-12 | 61.8 | 560 |
| 2-13 | 59.3 | 561 |
| 2-14 | 53.2 | 563 |
| 2-15 | 68.2 | 560 |
| 2-16 | 66.3 | 561 |
Synthesis Example 3
Synthesis of Compound 2-1
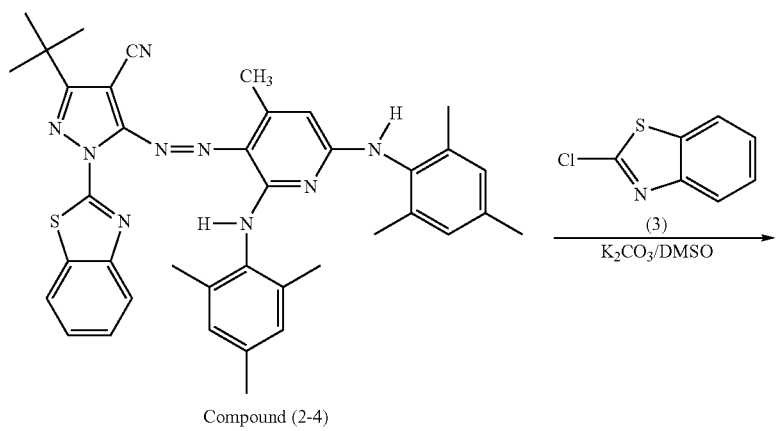
Compound (2-4)
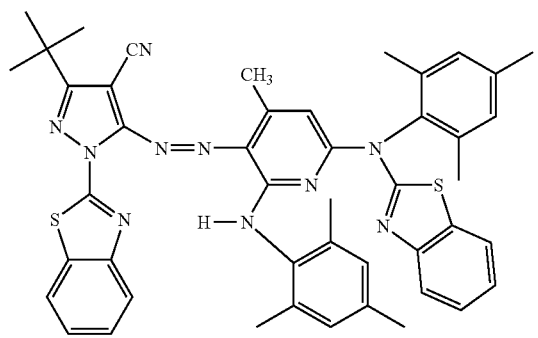
Compound (2-1)

To 37.3 g (56 mmol) of compound 2-4 were added 18.9 g (112 mmol) of 2-chlorobenzothiazole (heterylating agent 3), 20 g of potassium carbonate, and 210 ml of dimethyl sulfoxide (DMSO), and the mixture was heated at 100° C. for 4 hours with stirring while bubbling with nitrogen. After completion of the reaction, the reaction mixture was cooled to room temperature. The precipitate thus formed was collected by suction filtration, and the resulting crystals were washed with 200 ml of DMSO. The crystals were dispersed in 1500 ml of water, filtered by suction, and washed with water to give 29 g (65%) of compound 2-1.

$\lambda_{max}$=558 nm (DMF solution) m/z (positive ion mode)=802

Synthesis Example 4

Synthesis of Compound 6-4

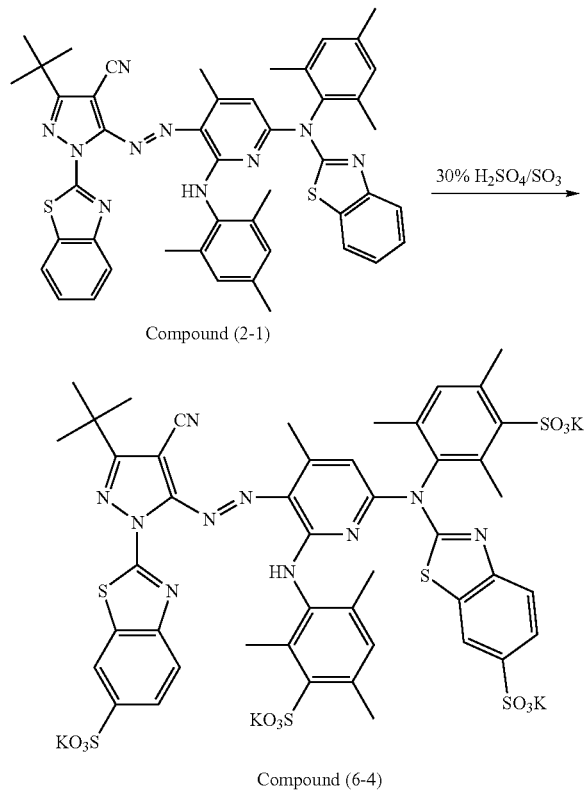

Compound (2-1)

Compound (6-4)

In a three-necked flask was put 90 ml of 30% fuming sulfuric acid and kept at around 15° C., and 30 g (37.5 mmol) of compound 2-1 was added thereto in divided portions over 30 minutes. After the addition, the mixture was stirred vigorously to be allowed to react at an inner temperature of 20° C. for 5 hours. The reaction mixture was cooled to 5° C., and 10 ml of pure water was added thereto dropwise with care so that the reaction temperature might not exceed 30° C. The reaction mixture was slowly added dropwise to 800 ml of a cold saturated aqueous solution of sodium chloride to precipitate crude crystals. At the same time a thick aqueous solution of sodium hydroxide (70 g of NaOH in 200 ml of pure water) was added dropwise to the reaction system. During the addition, the inner temperature of the system was kept at 40° C. or lower. The precipitate was collected by filtration and washed with 300 ml of a saturated sodium chloride aqueous solution. The Zresulting crude product 6-4 was dissolved in 600 ml of a 1/1 (by volume) mixture of methanol and ethanol, and the solution was filtered while hot. To the filtrate was added dropwise a solution of potassium acetate in 120 ml of a 1/1 (by volume) mixture of methanol and ethanol to conduct recrystallization, followed by filtration. The collected crystals were desalted through a membrane to give 35 g (72.3%) of compound 6-4 with high purity.

$\lambda_{max}$=560 nm (DMSO)

Synthesis Example 5

Compounds shown in Table 12 were synthesized in the same manner as in Synthesis Example 4. The reaction results are also shown in the Table.

TABLE 12

| Dye | Yield (%) | $\lambda_{max}$ (nm) in DMSO |
| --- | --- | --- |
| 6-1 | 73 | 548 |
| 6-2 | 62 | 550 |
| 6-3 | 61 | 544 |
| 6-4 | 78 | 555 |
| 6-5 | 70 | 556 |
| 6-6 | 65 | 558 |
| 7-1 | 80 | 560 |
| 7-2 | 73 | 562 |
| 7-3 | 75 | 559 |
| 7-4 | 68 | 555 |
| 7-5 | 63 | 558 |
| 7-6 | 75 | 560 |
| 7-7 | 77 | 557 |
| 7-8 | 79 | 560 |
| 7-9 | 78 | 561 |
| 7-10 | 70 | 560 |

Synthesis Example 6

Synthesis of Compound 2-1

1) Synthesis of Compound 4-5

A mixture of 7.55 g (46 mmol) of 5-amino-3-t-butyl-4-cyanopyrazole (1), 15 ml of concentrated hydrochloric acid, and 20 ml of a 2/3 (by volume) mixture of acetic acid and propionic acid was stirred at an inner temperature of 5° C., and a solution of 3.36 g (48 mmol) of sodium nitrite in 10 ml of water was added thereto in divided portions over 10 minutes. After the addition, the stirring was continued for an additional 10 minute period to form a diazonium salt.

Separately, 100 ml of pyridine was added to 20.0 g (44 mmol) of coupling component (2) in a three-necked flask, and the mixture was stirred and cooled to an inner temperature of 5° C. The diazonium salt was put into the three-necked flask over 10 minutes. After stirring the mixture for 30 minutes, the reaction mixture was poured into a mixture of 110 ml of a 1N hydrochloric acid aqueous solution and 600 g of ice. The precipitate was collected by filtration by suction to isolate 26.2 g (88%) of compound 4-5.

2) Synthesis of Compound 2-1

To 30.0 g (56 mmol) of compound 4-5 were added 58.4 ml (224 mmol) of 2-chlorobenzothiazole (heterylating agent 3), 62 g of potassium carbonate, and 210 ml of DMSO, and the mixture was stirred at 100° C. for 4 hours while bubbling with nitrogen. After completion of the reaction, the reaction mixture was cooled to room temperature. The precipitate thus formed was collected by suction filtration and washed with 200 ml of DMSO. The resulting crude crystals were dispersed in 1500 ml of water, filtered by suction, and washed with water to yield 63 g (80%) of compound 2-1.

$\lambda_{max}$=558 nm (DMF solution) m/z (positive ion mode)=802

Compound 2-1 was synthesized in the same manner as described above, except that nitrogen bubbling was not conducted. As a result, the yield was 45%.

Synthesis Example 7

Synthesis of Compound 2-1

To 37.3 g (56 mmol) of compound 2-4 were added 18.9 g (112 ml) of 2-chlorobenzothiazole (heterylating agent 3), 20 g of potassium carbonate, and 210 ml of DMSO, and the mixture was stirred at 100° C. for 4 hours while bubbling with nitrogen. After completion of the reaction, the reaction mixture was cooled to room temperature. The precipitate thus formed was collected by suction filtration and washed with 200 ml of DMSO. The resulting crude crystals were dispersed in 1500 ml of water, filtered by suction, and washed with water to give 29 g (65%) of compound 2-1.

$\lambda_{max}$=558 nm (DMF solution) m/z (positive ion mode)=802

Compound 2-1 was synthesized in the same manner as described above, except that nitrogen bubbling was not conducted. As a result, the yield was 50%.

The results of Synthesis Examples 6 and 7 reveal that reaction in an oxygen-free atmosphere brings about better results in yield.

Example 1

Preparation of Water-Based Ink

The following components were mixed, heated at 30 to 40° C. for 1 hour while stirring, and filtered under pressure through a microfilter with an average pore size of 0.8 µm and a diameter of 47 mm to prepare ink composition A.

Formulation of Ink Composition A:

| | |
|---|---|
| Compound 2-13 | 5 parts |
| Diethylene glycol | 9 parts |
| Tetraethylene glycol monobutyl ether | 9 parts |
| Glycerol | 7 parts |
| Diethanolamine | 2 parts |
| Water | 70 parts |

Ink compositions B to H were prepared in the same manner as for ink composition A, except for replacing compound 2-13 with the dye shown in Table 13 below.

Image Recording and Evaluation

An image was recorded on photo glossy paper (Super Photo Grade, available from Fuji Photo Film Co., Ltd.) on an ink jet printer (PM-700C, available from Seiko Epson Corp.) by using each of ink compositions A to H. The resulting image was evaluated for hue, light fastness, and ozone resistance as follows. The results obtained are shown in Table 13.

1) Hue

The hue was observed with the naked eye and graded on an A-to-C scale. A means "excellent", B "good", and C "poor".

2) Light Fastness

The image density immediately after recording (initial density: $C_i$) was measured with a reflection densitometer X-Rite 310TR. After the image was exposed to xenon light (85,000 lux) for 7 days in a weather-o-meter (Atlas Ci65, from Atlas Electric Devices Co.), the image density ($C_f$) was again measured at three points whose initial densities were 1, 1.5, and 2.0. A dye retention (%) was calculated from the following equation:

$$\text{Dye retention (\%)} = [(C_i - C_f)/C_i] \times 100$$

An image having a dye retention of 80% or higher at every measuring point was graded A. An image having a dye retention lower than 80% at one or two out of three points was graded B. An image having a dye retention lower than 80% at every point was graded C.

3) Ozone Resistance

The recorded image was left to stand in a chamber having an ozone gas concentration of 0.5 ppm for 24 hours. A dye retention after exposure to ozone was obtained in the same manner as for evaluation of light fastness. The ozone concentration in the chamber was set with an ozone gas monitor (OZG-EM-01, available from Applics Co., Ltd.). An image having a dye retention of 70% or higher at every measuring point was graded A. An image having a dye retention lower than 70% at one or two out of three points was graded B. An image having a dye retention lower than 70% at every point was graded C.

TABLE 13

| Ink | Dye | Hue | Light Fastness | Ozone Resistance | Remark |
|---|---|---|---|---|---|
| A | 2-13 | A | A | A | Invention |
| B | 2-14 | A | A | A | " |
| C | 2-15 | A | A | A | " |
| D | 2-16 | A | A | A | " |
| E | (a) | A–B | C | C | Comparison |
| F | (b) | B–C | B | C | " |
| G | (c) | B | B | B | " |
| H | (d) | A–B | A–B | C | " |

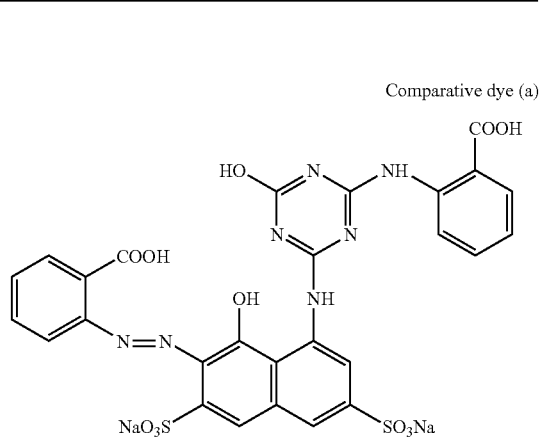

Comparative dye (a)

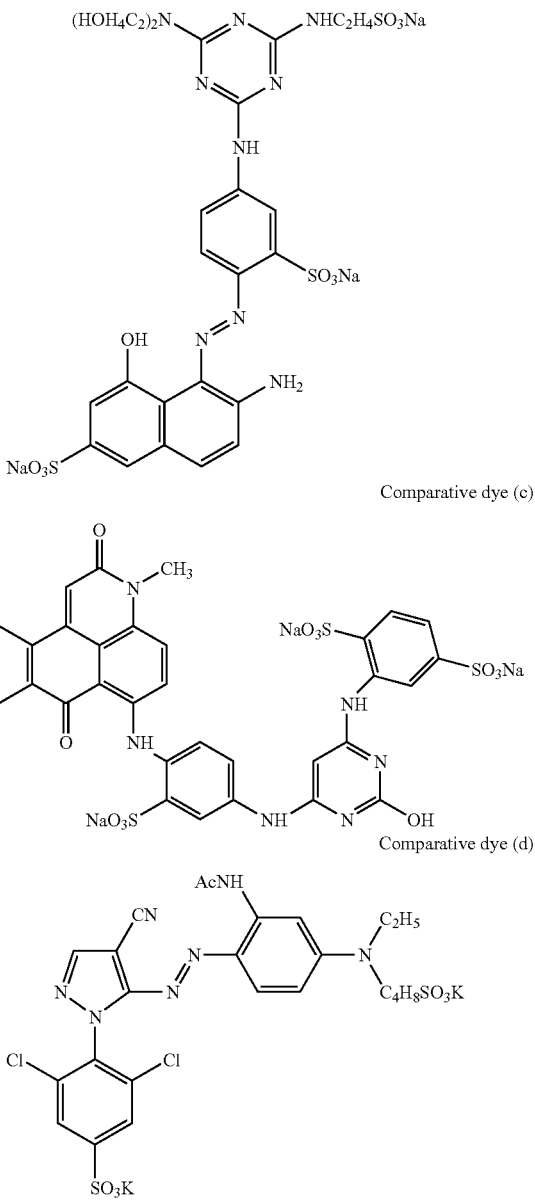

Comparative dye (b)

Comparative dye (c)

Comparative dye (d)

As is seen from Table 13, the magenta images printed in ink compositions A to D are clearer than those printed in ink compositions E to H. In addition, the images printed in ink compositions A to D were excellent in light fastness.

Further, super fine glossy paper (MJA4S3P, available from Seiko Epson) was printed on the same ink jet printer (PM-700C, from Seiko Epson) by using ink compositions A to D. Evaluation of the resulting images for hue and light fastness gave satisfactory results similar to those shown in Table 13.

Example 2

Preparation of Ink Sample 101

Azo compound 2-8 (oil-soluble) (5.63 g) and 7.04 g of sodium dioctylsulfosuccinate were dissolved in a mixture of 4.22 g of high-boiling organic solvent S-2 (shown below), 5.63 g of high-boiling organic solvent S-11 (shown below), and 50 ml of ethyl acetate at 70° C. To the solution was added 500 ml of deionized water while stirring with a magnetic stirrer to prepare an oil-in-water coarse dispersion, which was passed through Microfluidizer (available from Microfluidics Inc.) under a pressure of 600 bar five times. The solvent was removed from the resulting emulsion on a rotary evaporator until no smell of ethyl acetate was felt. The resulting fine emulsion of the hydrophobic dye was mixed with 140 g of diethylene glycol, 50 g of glycerol, 7 g of Surfynol 465 (available from Air Products & Chemicals, Inc.), and 900 ml of deionized water to prepare ink sample 101.

S-2:

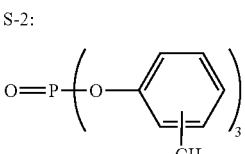

S-11:

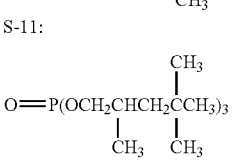

Preparation of Ink Samples 102 to 105

Ink samples 102 to 105 were prepared in the same manner as for ink sample 101, except for replacing the oil-soluble compound 2-8 with the oil-soluble compound shown in Table 14 below. The volume average particle size of the sample emulsions was measured with an ultrafine particle size analyzer Microtrack UPA (available from Nikkiso Co., Ltd.). The results obtained are shown in Table 14.

Image Recording and Evaluation

An image was recorded on photo glossy paper (Ink Jet Paper Photo Grade, available from Fuji Photo Film) on an ink jet printer (PM-700 from Seiko Epson) by using each of ink samples 101 to 105 and comparative ink compositions E to H prepared in Example 1. The recorded images were evaluated for tone, paper independence, water resistance, light fastness, and ozone resistance according to the following methods. The results obtained are shown in Table 15.

1) Tone

A reflection spectrum of the image was measured in a region of 390 to 730 nm at a 10 nm wavelength interval, and a* and b* values were calculated based on the CIE 1976 L*a*b* color space system. A preferred magenta tone was defined as follows.

Preferred a* value: 76 or greater
Preferred b* value: −30 to 0
A: Both a* and b* values are within the respective preferred ranges.
B: One of a* and b* values is within its preferred range.
C: Both a* and b* values are out of the respective preferred ranges.

2) Paper Independence

The tone of the image formed on the photo glossy paper and that of an image separately formed on paper for plain paper copiers (PPCs) were compared. A small difference between the two, which indicates small paper dependence, was graded A (satisfactory), and a large difference was graded B (poor).

3) Water Resistance

The photo glossy paper having an image formed thereon was dried at room temperature for 1 hour, then soaked in water for 30 seconds, and dried spontaneously at room temperature. Feathering of the ink image was observed, and water resistance of the ink was graded A (no feathering), B (slight feathering) or C (considerable feathering).

4) Light Fastness

The image formed on the photo glossy paper was exposed to xenon light (85,000 lux) for 3 days in a weather-o-meter (Ci65 from Atlas). A dye retention was obtained in the same manner as in Example 1. An image having a dye retention of 70% or higher at every measuring point was graded A. An image having a dye retention lower than 70% at one or two out of three points was graded B. An image having a dye retention lower than 70% at every point was graded C.

5) Ozone Resistance

The same test method and grading system as used in Example 1 were followed.

TABLE 14

| Sample | Dye | Average Particle Size (nm) |
|---|---|---|
| 101 | 2-8 | 55 |
| 102 | 2-9 | 48 |
| 103 | 2-10 | 63 |
| 104 | 2-11 | 58 |
| 105 | 2-12 | 70 |

TABLE 15

| Sample | Tone | Paper Independence | Water Resistance | Light Fastness | Ozone Resistance |
|---|---|---|---|---|---|
| 101 | A | A | A | A | A |
| 102 | A | A | A | A | A |
| 103 | A | A | A | A | A |
| 104 | A | A | A | A | A |
| 105 | A | A | A | A | A |
| E | A–B | B | B | B | C |
| F | B | B | B | A–B | C |
| G | B | B | B | B | C |
| H | A–B | B | B | A–B | C |

As is apparent from the results in Table 15, the ink-jet ink compositions according to the present invention are excellent in color tone, paper independence, water resistance, and light fastness.

Example 3

Ink jet printing was carried out on photo glossy paper GP-301 (available from Canon Inc.) with an ink jet printer BJ-F850 (from Canon Inc.) loaded with an ink cartridge filled with each of the ink compositions prepared in Example 2. The results of evaluation of the images were as satisfactory as those obtained in Example 2.

Example 4

Preparation of Water-Based Ink

Deionized water was added to a mixture of the following components to make one liter, and the mixture was stirred at 30 to 40° C. for 1 hour. If necessary, the pH of the mixture was adjusted to 9 with a 10 mol/l aqueous solution of potassium hydroxide. The mixture was filtered through a microfilter with an average pore size of 0.25 μm under reduced pressure to prepare a magenta ink composition I.

Formulation of Ink Composition I:

| | |
|---|---|
| Azo compound 2-17 | 8.5 g/l |
| Diethylene glycol | 150 g/l |
| Urea | 37 g/l |
| Glycerol | 130 g/l |
| Triethylene glycol monobutyl ether | 130 g/l |
| Triethanolamine | 6.9 g/l |
| Benzotriazole | 0.08 g/l |
| Surfynol 465 | 10 g/l |
| Proxel XL2 | 3.5 g/l |

Ink compositions J to P were prepared in the same manner as for ink composition I, except for replacing compound 2-17 with the compound shown in Table 16 below. Comparative dyes (a), (b), (c), and (d) shown in Table 16 are the same as used in Example 1.

Image Recording and Evaluation

Ink jet printing was carried out on photo glossy paper EX (available from Fuji Photo Film) with an ink jet printer PM-670C (available from Seiko Epson) loaded with an ink cartridge filled with each of the ink compositions I to P prepared above. The images were evaluated for hue, paper independence, water resistance, light fastness, and ozone resistance as follows. The results obtained are shown in Table 16.

1) Hue

Evaluated and graded in the same manner as in Example 1.

2) Paper Independence

Evaluated and graded in the same manner as in Example 2.

3) Water Resistance

The photo glossy paper having formed thereon an image having a reflection density of about 1.0 was dried at room temperature for 1 hour, then soaked in ion-exchanged water for 3 minutes, and dried spontaneously at room temperature. Water resistance of the ink image was evaluated from density change and graded on an A-to-C scale as follows.

A: Substantially no change was observed.
B: Reduction in density was observed.
C: Considerable reduction in density was observed.

The same test was carried out for images formed on plain paper for PPCs.

4) Light Fastness

The same test method and grading system as used in Example 1 were followed.

5) Ozone Resistance

The recorded image was left to stand in a chamber having an ozone gas concentration of 0.5 ppm for 7 days. A dye retention after exposure to ozone was obtained in the same manner as for evaluation of light fastness. The ozone concentration in the chamber was set with an ozone gas monitor (OZG-EM-01, available from Applics Co., Ltd.). An image having a dye retention of 80% or higher at every measuring point was graded A. An image having a dye retention lower than 80% at one or two out of three points was graded B. An image having a dye retention lower than 80% at every point was graded C.

TABLE 16

| Sample | Dye | Hue | Water Resistance | | | Light Fastness | Ozone Resistance |
| | | | Paper Independence | Photo Glossy Paper | Plain Paper | | |
|---|---|---|---|---|---|---|---|
| I | 2-17 | A | A | A | A | A | A |
| J | 2-18 | A | A | A | A | A | A |
| K | 2-19 | A | A | A | A | A | A |
| L | 2-20 | A | A | A | A | A | A |
| M | (a) | A | B | B | C | C | C |
| N | (b) | C | B | B | C | B | C |
| O | (c) | B | B | B | C | B | C |
| P | (d) | A | B | B | C | A | C |

Table 16 shows that the magenta images printed in ink compositions I to L are clearer than those printed in ink compositions M to P. In addition, the images printed in ink compositions I to L were excellent in light fastness and ozone resistance.

Example 5

Ink jet printing was carried out on photo glossy paper (KA420PSK, available from Seiko Epson) on an ink jet printer (PM-670C, from Seiko Epson) by using the ink compositions I to L prepared in Example 4. The results of evaluation of the resulting images in terms of hue, paper independence, water resistance, light fastness and ozone resistance were as satisfactory as those obtained in Example 4.

Example 6

Ink jet printing was carried out on photo glossy paper (GP-301, available from Canon Inc.) with an ink jet printer (BJ-F850, from Canon) loaded with an ink cartridge filled with each of the ink compositions I to L. The resulting images were evaluated in the same manner as in Example 4. The results were as satisfactory as those obtained in Examples 4 and 5.

The present invention provides a novel dye compound having absorption characteristics with excellent color reproducibility as one of three primary colors and sufficient fastness against light, heat, humidity, and active gases in the environment and a process of producing the same.

The invention also provides coloring compositions providing color images or coloring materials excellent in hue and fastness in broad applications, such as printing ink compositions for, for example, ink jet printing; ink sheets used in thermal transfer image forming materials; toners for electrophotography; coloring compositions for color filters used in LCDs and CCDs; and dye baths for textile.

The invention also provides an ink-jet ink composition capable of forming an image with a satisfactory hue and high fastness to light and active gases in the environment, especially ozone.

Example 7

1) Synthesis of Compound 2-1-1:

2,6-Dichloro-3-cyano-4-methylpyridine (10.0 g, 53.4 mmol) and 32.5 g (240.3 mmol) of 2,4,6-trimethylaniline were stirred at an inner temperature of 160° C. for 6 hours. To the reaction mixture was added 300 ml of ethyl acetate, and stirring was continued for an additional 30 minute period. Any insoluble matter was removed by filtration, and ethyl acetate was removed by evaporation. The residue was crystallized from hexane to give 13.4 g of compound 2-1-1 in a yield of 65%.

m/z (FAB-MS; positive ion mode)=384

2) Synthesis of Compound 2-1-11

To 10.0 g (26.0 mmol) of compound 2-1-1 were added 25.0 g of phosphoric acid and 25.0 g of polyphosphoric acid, and the mixture was stirred at an inner temperature of 160° C. for 6 hours. Ethyl acetate was added to the reaction mixture at room temperature, and the ethyl acetate solution was poured into 1 liter of ice-water, neutralized with sodium hydrogencarbonate, and subjected to liquid-liquid separation. The organic layer was washed with water and dried over anhydrous sodium sulfate. The inorganic matter was separated by filtration, and the organic layer was concentrated. Hexane was added to the residue to. reprecipitate the desired product, which was recrystallized from a hexane/isopropyl alcohol (IPA) mixed solvent to give white crystals of compound 2-1-11 in a yield of 95%.

m/Z (FAB-MS; positive ion mode)=358

3) Synthesis of Compound 2-1-2

2,6-Dichloro-3-cyano-4-methylpyridine (10.0 g, 53.4 mmol) and 58.9 g (240.3 mmol) of 4-n-octylaniline were stirred at an inner temperature of 160° C. for 6 hours. To the reaction mixture was added 300 ml of ethyl acetate, followed by stirring for 30 minutes. Any insoluble matter was removed by filtration, and ethyl acetate was removed by evaporation. Hexane was added to the residue, and the precipitated solid was collected by filtration to give 27.8 g (82%) of compound 2-1-2.

m/Z (FAB-MS; positive ion mode)=524 $^1$H-NMR (CDCl$_3$) δ: 0.881 (t, J=6.48 Hz, 6H, CH$_3$CH$_2$—), 1.275-1.314 (m, 20H, CH$_3$—C$_5$H$_{10}$—CH$_2$—), 1.570-1.613 (m, 4H, Ar—CH$_2$—CH$_2$—), 2.330 (s, 3H, —CH$_3$), 2.590 (t, J=7.44 Hz, 4H, Ar—CH$_2$—), 6.032 (s, 1H, —H), 6.547 (s, 1H, Ar—NH—), 6.842 (s, 1H, Ar—NH—), 7.127 (d, J=8.22 Hz, 4H, Ar—H), 7.202 (d, J=8.46 Hz, 2H, Ar—H), 7.436 (d, J=8.43 Hz, 2H, Ar—H).

83
Example 8
1) Synthesis of Azo Compound 2-2-1
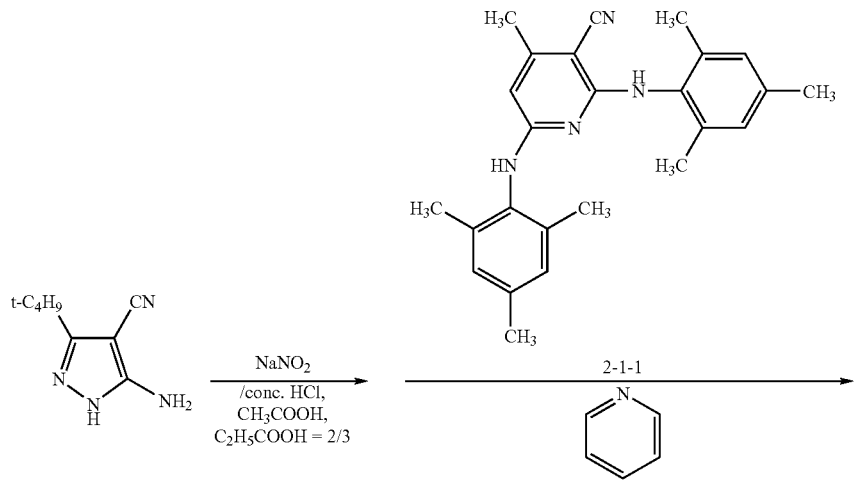
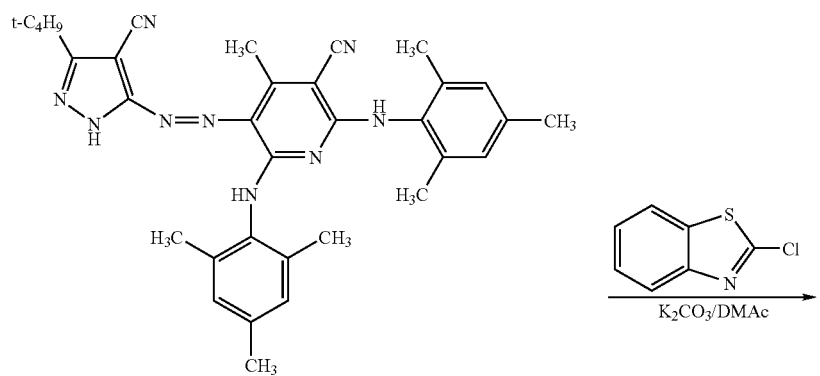
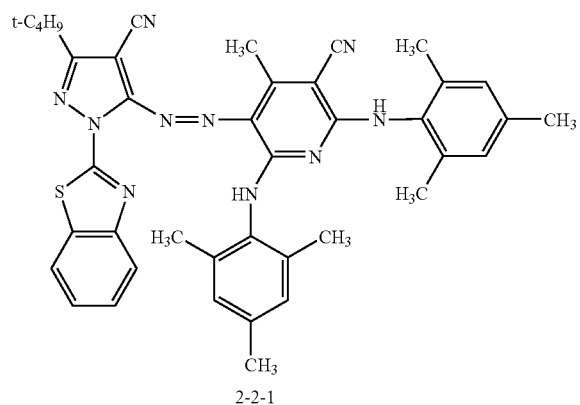
2-2-1

5-Amino-3-t-butyl-4-cyanopyrazole (8 g, 48.7 mmol), 15 ml of concentrated hydrochloric acid, and 15 ml of a 2/3 (by volume) mixture of acetic acid and propionic acid were stirred at an inner temperature of 5° C. To the mixture was added 3.36 g (48.7 mmol) of sodium nitrite in divided portions over 10 minutes, followed by stirring for 10 minutes. The resulting diazonium salt solution was added dropwise to 100 ml of a pyridine solution containing 21.3 g (40.6 mmol) of compound 2-1-1 at an inner temperature of 10° C. or lower. After completion of the dropwise addition, the reaction mixture was stirred at that temperature for 30 minutes. The reaction mixture was poured into 1 liter of ice-water. The precipitated azo compound was collected by filtration by suction and reprecipitated from an EPA/methanol mixed solvent.

The resulting azo compound (15.4 g, 40 mmol), 17.0 g (50 ml) of 2-chlorobenzothiazole, and 5.5 g of potassium carbonate were suspended in 100 ml of dimethylacetamide (DMAc) and heated at 100° C. for 1 hour while stirring. After completion of the reaction, the reaction mixture was cooled to room temperature, and 400 ml of a saturated aqueous solution of sodium chloride was added thereto. The precipitate thus formed was collected by filtration by suction and recrystallized from acetonitrile to afford 25.6 g (80%) of azo compound 2-2-1.

$\lambda_{max}$=532 nm (dimethylformamide (DMF) solution) m/z (positive ion mode)=692

2) Synthesis of Azo Compound 2-2-11

2-1) Synthesis with DMF as Solvent for Compound (2-I) and Sodium Acetate as Base for Coupling

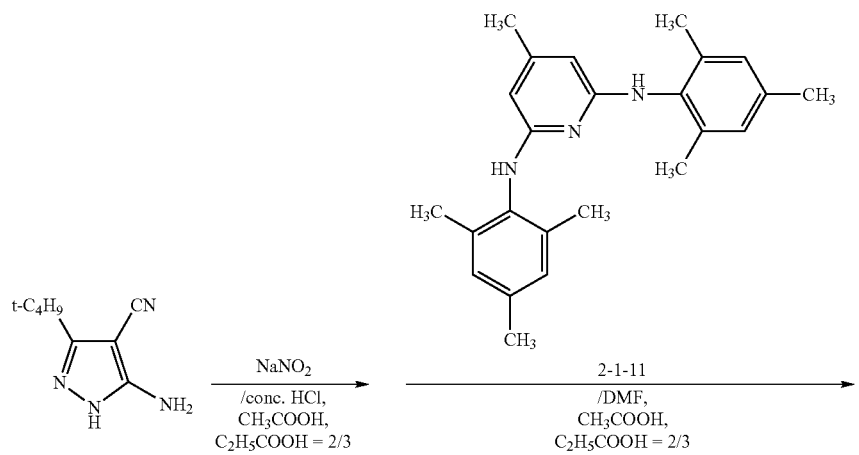

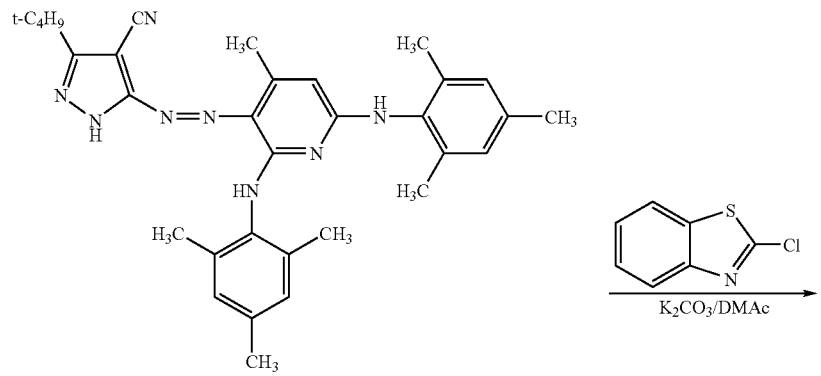

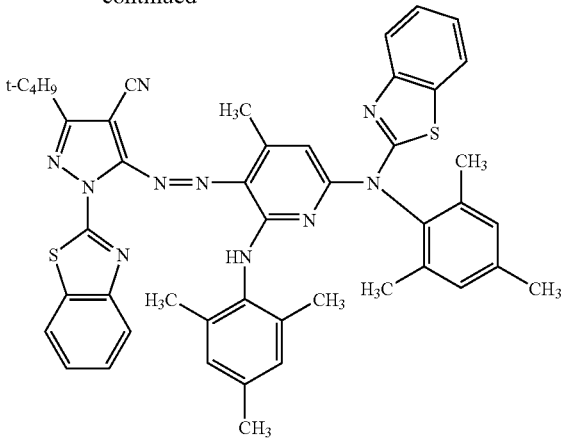

2-2-11

Eight grams (48.7 mmol) of 5-amino-3-t-butyl-4-cyanopyrazole, 15 ml of concentrated hydrochloric acid, and 15 ml of a 2/3 (by volume) mixture of acetic acid/propionic acid were stirred at an inner temperature of 5° C., and 3.36 g (48.7 mmol) of sodium nitrite was added thereto in divided portions over 10 minutes, followed by stirring for 10 minutes. The resulting diazonium salt solution was added dropwise to a solution of 21.3 g (40.6 mmol) of compound 2-1-11 and 50.0 g of sodium acetate in 200 ml of a mixed organic solvent (100 ml of DMF and 100 ml of acetic acid/propionic acid=2/3 by volume) at an inner temperature of 10° C. or lower. After the addition, the reaction mixture was stirred at that temperature for 30 minutes and poured into 1 liter of ice-water. The azo compound thus precipitated was collected by suction filtration and reprecipitated in IPA/methanol.

In 100 ml of DMAc were suspended 22.4 g (40 mmol) of the resulting azo compound, 17.0 g (50 ml) of 2-chlorobenzothiazole, and 5.5 g of potassium carbonate and heated at 100° C. for 1 hour while stirring. After completion of the reaction, the reaction mixture was cooled to room temperature, and 400 ml of a saturated aqueous solution of sodium chloride was added thereto. The precipitate thus formed was collected by filtration by suction and recrystallized from acetonitrile to give 26.3 g (82%) of azo compound 2-2-11.

$\lambda$=558 nm (DMF solution) m/z (positive ion mode)=802

2-2) Synthesis with Acetic Acid/Propionic Acid as Solvent for Compound (2-I) and Triethylamine as Base A diazonium salt solution was prepared in the same manner as in (2-1) above. The resulting diazonium salt solution was added dropwise to a solution of 21.3 g (40.6 mmol) of compound 2-1-11 and 100 ml of triethylamine in 330 ml of a mixed organic solvent of acetic acid/propionic acid (2/3 by volume) at an inner temperature of 10° C. or lower. After the addition, the reaction mixture was stirred at that temperature for 30 minutes and poured into a 1N HCl aqueous solution. The azo compound thus precipitated was collected by suction filtration and reprecipitated in IPA/methanol.

The resulting azo compound was heterylated with 2-chlorobenzothiazole in the same manner as in (2-1) above to give 22.5 g (70%) of azo compound 2-2-11.

$\lambda_{max}$=558 nm (DMF solution) m/z (positive ion mode)=802

2-3) Synthesis with Pyridine as Solvent for Compound (2-I) and Base

A diazonium salt solution was prepared in the same manner as in (2-1) above. The resulting diazonium salt solution was added dropwise to 60 ml of a pyridine solution containing 21.3 g (40.6 mmol) of compound 2-1-11 at an inner temperature of 10° C. or lower.

After the addition, the reaction mixture was stirred at that temperature for 30 minutes and poured into a 1N HCl aqueous solution. The azo compound thus precipitated was collected by suction filtration and reprecipitated in IPA/methanol.

The resulting azo compound was heterylated with 2-chlorobenzothiazole in the same manner as in (2-1) above to give 29.8 g (93%) of azo compound 2-2-11.

$\lambda_{max}$=558 nm (DMF solution) m/z (positive ion mode)= 802

As is recognized from comparison among the synthesis procedures (2-1), (2-2), and (2-3), the azo compound according to the invention is produced in a higher yield when the procedure (2-3) is followed. For better understanding the reaction results of Example 8 are shown in Table 2-6.

TABLE 2-6

| Synthesis Procedure | Yield (%) |
| --- | --- |
| (2-1) | 82 |
| (2-2) | 70 |
| (2-3) | 93 |

Example 9

1) Synthesis of Azo Compound 2-3-1

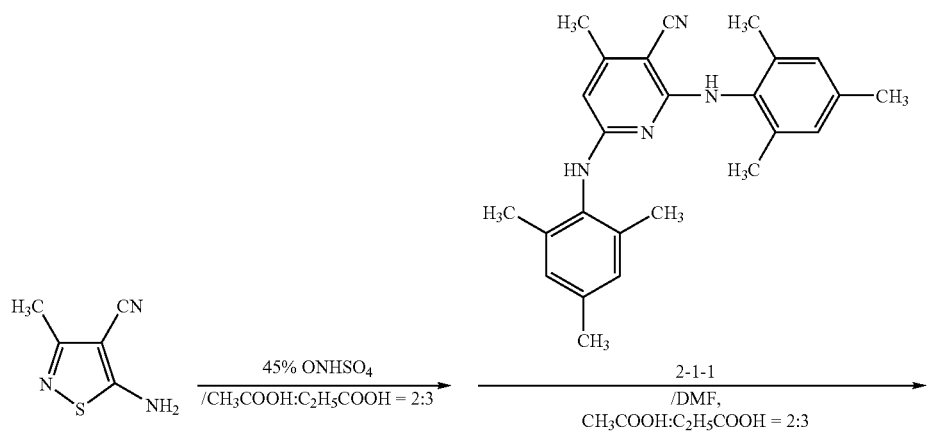

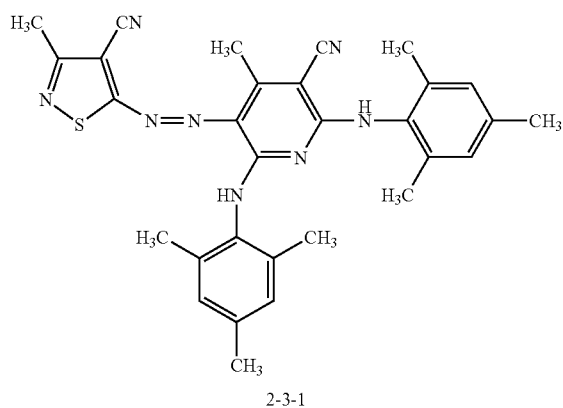

2-3-1

5-Amino-4-cyano-3-methylisothiazole (0.25 g, 1.8 mmol), 1.2 ml of acetic acid, and 1.8 ml of propionic acid were stirred at an inner temperature of 0° C. or lower, and 0.6 g (1.98 mmol) of 45% nitrosylsulfuric acid was added thereto. The mixture was stirred at that temperature for 30 minutes to prepare a diazonium salt. In a separate flask, 0.54 g (1.5 mmol) of compound 2-1-1, 2.4 g of sodium acetate, 13.5 ml of DMF, and 6 ml of ethyl acetate were stirred and cooled to an inner temperature of 0° C. or lower. The diazonium salt was added to the solution, and the mixture was stirred at that temperature for 2 hours. To the reaction mixture was added 30 ml of a saturated sodium chloride aqueous solution, and the precipitate formed was collected by filtration by suction. The crude crystals were purified by silica gel column chromatography (hexane/ethyl acetate) to give 0.05 g (55%) of azo compound 2-3-1.

$\lambda_{max}$=529 nm (DMF solution) m/z (FAB-MS; negative ion mode)=509

Example 10

Compounds of the present invention shown in Table 2-7 below were synthesized in the same manner as in Example 7, and azo compounds shown in Table 2-7 were synthesized therefrom in accordance with a procedure equivalent to that of Examples 8 or 9.

Evaluation of Hue:

Each of the azo compounds prepared by using the compounds of the invention and comparative dyes 2-1 to 2-4 shown below was dissolved in DMF in a concentration adjusted so as to give an absorbance of 1.000 at the $\lambda_{max}$ in the magenta region as measured with a UV spectrum meter supplied by Shimadzu Corp. The UV spectrum of each solution was measured with the same equipment, and a half-value width in the magenta region (the width of the absorption band at an absorbance of 0.500) was obtained. The half-value width thus calculated was rated as follows.

A . . . 75 nm or narrower
B . . . 76 to 85 nm
C . . . 86 to 95 nm
D . . . 96 nm or wider The results obtained are shown in Table 2-7.

Comparative Dye 2-1:

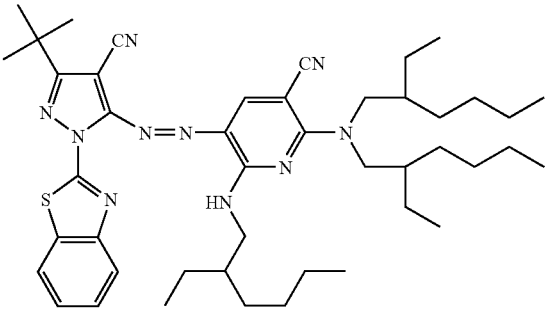

Comparative Dye 2-2:

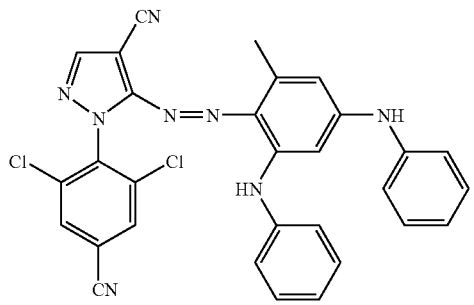

Comparative Dye 2-3:

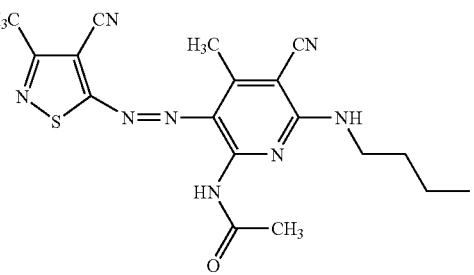

Comparative Dye 2-4:

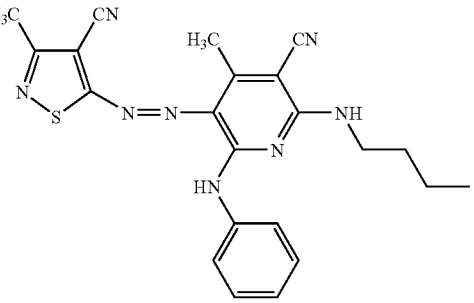

TABLE 2-7

| Compound of Invention | Synthesis Procedure | Azo Compound | Yield (%) | $\lambda_{max}$/DMF | Half-value With (nm) | Evaluation Result | Remark |
|---|---|---|---|---|---|---|---|
| 2-1-1 | Example 8 (2-3) | 2-2-1 | 80 | 532 | 80 | A | invention |
| 2-1-4 | Example 8 (2-3) | 2-2-4 | 67 | 554 | 84 | A | invention |
| 2-1-6 | Example 8 (2-3) | 2-2-6 | 69 | 552 | 83 | A | invention |
| 2-1-11 | Example 8 (2-3) | 2-2-11 | 93 | 545 | 83 | A | invention |
| 2-1-12 | Example 8 (2-3) | 2-2-12 | 73 | 543 | 91 | B | invention |
| 2-1-23 | Example 8 (2-3) | 2-2-23 | 85 | 556 | 83 | A | invention |
| 2-1-24 | Example 8 (2-3) | 2-2-24 | 68 | 565 | 82 | A | invention |
| 2-1-1 | Example 9 | 2-3-1 | 55 | 529 | 81 | A | invention |
| — | — | Dye 2-1 | 72 | 540 | 95 | C | comparison |
| — | — | Dye 2-2 | 71 | 560 | 111 | D | comparison |
| — | — | Dye 2-3 | 57 | 510 | 101 | D | comparison |
| — | — | Dye 2-4 | 60 | 523 | 107 | D | comparison |

As can be seen from Table 2-7, the azo compounds prepared by using the compounds of the present invention show a sharper absorption band with a narrower half-value width than the comparative dyes.

The present invention provides a novel compound capable of providing an azo compound having excellent color reproducibility as a dye of three primary colors and sharp absorption characteristics with a narrow half-value width. The present invention also provides a process of producing such an azo compound in a high yield.

The entire disclosure of each and every foreign patent application from which the benefit of foreign priority has been claimed in the present application is incorporated herein by reference, as if fully set forth.

What is claimed is:

1. A compound represented by the following formula (2-I):

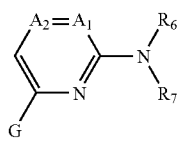

(2-I)

wherein $A_1$ represents —$CR_1$= and $A_2$ represents —$CR_2$= or a nitrogen atom; at least one of $R_6$ and $R_7$ represents an aromatic group or a heterocyclic group with the other representing a hydrogen atom, an aliphatic group, an aromatic group, a heterocyclic group, an acyl group, an alkoxycarbonyl group, an aryloxycarbonyl group or a sulfamoyl group, wherein each group may have a substituent; G represents an amino group substituted with an aromatic group or a heterocyclic group; $R_1$ and $R_2$ each independently represent a hydrogen atom, a halogen atom, an aliphatic group, an aromatic group, a heterocyclic group, a cyano group, a carboxyl group, a carbamoyl group, an alkoxycarbonyl group, an aryloxycarbonyl group, an acyl group, a hydroxyl group, an alkoxy group, an aryloxy group, a silyloxy group, an acyloxy group, a carbamoyloxy group, a heterocyclic oxy group, an alkoxycarbonyloxy group, an aryloxycarbonyloxy group, an amino group substituted with an alkyl group, an aromatic group or a heterocyclic group, an acylamino group, a ureido group, a sulfamoylamino group, an alkoxycarbonylamino group, an aryloxycarbonylamino group, an alkylsulfonylamino group, an arylsulfonylamino group, a nitro group, an alkylthio group, an arylthio group, a heterocyclic thio group, an alkylsulfonyl group, an arylsulfonyl group, an alkylsulfinyl group, an arylsulfinyl group, a sulfamoyl group or a sulfo group, wherein each group may have a substituent, wherein $R_1$ and $R_6$ are optionally taken together, or $R_6$ and $R_7$ are optionally taken together, each to form a 5- or 6-membered ring.

2. The compound according to claim 1 wherein the compound represented by the formula (2-I) is represented by the following formula (2II):

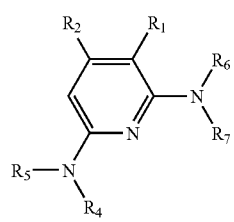

(2-II)

wherein $R_1$, $R_2$, $R_6$ and $R_7$ are as defined in the formula (2-I); and at least one of $R_4$ and $R_5$ represents an aromatic group or a heterocyclic group with the other representing a hydrogen atom, an aromatic group, a heterocyclic group, an acyl group, an alkoxycarbonyl group, an aryloxycarbonyl group, a carbamoyl group, a sulfonyl group or a sulfamoyl group, wherein $R_1$, $R_2$, $R_4$, $R_5$ and $R_6$ may each have a substituent.

3. A process for producing an azo compound comprising (1) forming a diazonium salt with a diazotizing agent, and (2) reacting the compound according to claim 1 with the diazonium salt to produce the azo compound, wherein the diazonium salt is an aromatic or heterocyclic compound having an amino group, and wherein the diazotizing agent is selected from the group consisting of a hydrochloric acid solution of sodium nitrite, a hydrochloric acid solution of isopentyl nitrite and nitrosylsulfuric acid;

wherein in the reacting step, pyridine is used as a solvent for the compound of formula (2-I).

4. A process for producing an azo compound comprising (1) forming a diazonium salt with a diazotizing agent, and (2) reacting the compound represented by the formula (2-II) according to claim 2 with the diazonium salt to produce the azo compound, wherein the diazonium salt is an aromatic or heterocyclic compound having an amino group, and wherein the diazotizing agent is selected from the group consisting of a hydrochloric acid solution of sodium nitrite, a hydrochloric acid solution of isopentyl nitrite and nitrosylsulfuric acid;

wherein in the reacting step, pyridine is used as a solvent for the compound of formula (2-II).

* * * * *